(12) United States Patent
Holt et al.

(10) Patent No.: US 10,302,611 B2
(45) Date of Patent: May 28, 2019

(54) HYDROGEN-SELECTIVE POROUS COMPOSITE

(71) Applicant: NexTech Materials Ltd., Lewis Center, OH (US)

(72) Inventors: Christopher T. Holt, Bexley, OH (US); Stephen R. Cummings, Worthington, OH (US); Scott L. Swartz, Columbus, OH (US); Lora B. Thrun, Grove City, OH (US)

(73) Assignee: NEXCERIS INNOVATION HOLDINGS, LLC, Lewis Center, OH (US)

( * ) Notice: Subject to any disclaimer, the term of this patent is extended or adjusted under 35 U.S.C. 154(b) by 240 days.

(21) Appl. No.: 14/691,420

(22) Filed: Apr. 20, 2015

(65) Prior Publication Data
US 2015/0226718 A1 Aug. 13, 2015

Related U.S. Application Data

(63) Continuation of application No. 11/974,520, filed on Oct. 12, 2007, now Pat. No. 9,011,778.
(Continued)

(51) Int. Cl.
*H01M 4/38* (2006.01)
*G01N 27/04* (2006.01)
(Continued)

(52) U.S. Cl.
CPC .......... *G01N 33/005* (2013.01); *G01N 27/04* (2013.01); *H01M 4/383* (2013.01);
(Continued)

(58) Field of Classification Search
CPC ..... G01N 33/005; G01N 27/04; H01M 4/383; H01M 8/04216; Y02E 60/364; Y02E 60/50
See application file for complete search history.

(56) References Cited

U.S. PATENT DOCUMENTS 4,015,230 A 3/1977 Nitta et al.
4,241,019 A 12/1980 Nakatani et al.
(Continued)

FOREIGN PATENT DOCUMENTS

EP 0653632 A1 5/1995
EP 1111703 A2 6/2001
JP 61003054 A 1/1986

OTHER PUBLICATIONS

Guo, Xin, Wilfried Sigle, and Joachim Maier. "Blocking Grain Boundaries in Yttria-Doped and Undoped Ceria Ceramics of High Purity." Journal of the American Ceramic Society 86.1 (2003): 77-87.*
(Continued)

*Primary Examiner* — Robert J Eom
(74) *Attorney, Agent, or Firm* — Benesch, Friedlander, Coplan & Aronoff LLP

(57) ABSTRACT

Provided are a composition including a hydrogen-selective porous composite, a hydrogen gas sensor device including the hydrogen-selective porous composite, a kit for detecting hydrogen including the hydrogen gas sensor device, and a method for detecting hydrogen including contacting a hydrogen-comprising gas to the hydrogen selective porous composite. The method may include, for example: providing a hydrogen-comprising gas; providing a hydrogen-selective porous composite, the hydrogen-selective porous composite comprising cerium oxide; contacting the hydrogen-comprising gas to the hydrogen-selective porous composite; and selectively detecting hydrogen in the hydrogen-comprising gas according to a decrease in an electrical resistance of the hydrogen-selective porous composite.

55 Claims, 33 Drawing Sheets

Step (1): Extrusion and Sintering of Support

Step (2): Deposition of Patterned Electrodes

Step (3): Deposition of Sensor Material Coating

Related U.S. Application Data

(60) Provisional application No. 60/851,220, filed on Oct. 12, 2006.

(51) Int. Cl.
   *G01N 33/00* (2006.01)
   *H01M 8/04082* (2016.01)

(52) U.S. Cl.
   CPC ....... *H01M 8/04216* (2013.01); *Y02E 60/364* (2013.01); *Y02E 60/50* (2013.01)

(56) References Cited

U.S. PATENT DOCUMENTS

| | | |
|---|---|---|
| 4,614,669 A | 9/1986 | Yannopoulous |
| 4,730,479 A | 3/1988 | Pyke et al. |
| 5,635,627 A | 6/1997 | Bytyn |
| 6,109,095 A | 8/2000 | Addiego |
| 6,202,471 B1 | 3/2001 | Yadav et al. |
| 2007/0141443 A1 | 6/2007 | Brown |

OTHER PUBLICATIONS

Sberveglieri, G. "Recent developments in semiconducting thin-film gas sensors." Sensors and Actuators B: Chemical23.2-3 (1995): 103-109.*

A.M. Azad et al., Hydrocarbon and sulfur sensors for SOFC systems, Phase I Final Report, DOE Contract No. DE-FC26-02NT41576, Nov. 2003, p. 1-32.

Lu et al, Micro-type powder-sputtered t hin film gas sensors with long term stabiity, Proceedings of the 2006 IEEE International Conference on Mchatronics and Automation, Jun. 25-28, 2006 China, pp. 2111-2115.

Zhang et al, Effect of tansition metal oxides on densification and electrical properties of Si-containing Ce 0.8 Gd 0.2 O2-δ ceramics, 2004, Elsevier B.V., Splod State Ionics, 168, pp. 187-195.

Borchert et al, Nanostructures, Gd-doped ceria promoted by Pt or Pd: investigation of the electronic and surface structures and relations to chemical properties, 2005, ACS, J Phys Chem B, 109, pp. 20077-20086.

Kim et al, Sensitivity enhancement for CO gas detection using Sn02—Ce02—PdOx system, 2004 Elsevier B.V., Sensiors and Actuators B 107, pp. 825-830.

Trinchi et al, Investigation of sol-gel prepared C3)2—TiO2 thin films for oxygen gas sensing, 2003 Elsevier B.V., Sensiors and Actuators B 95, pp. 145-150.

Katsuki et al, H2 selective gas sensor based on SnO2, 1998 Elsevier Science S.A., Sensors and Actuators B 52, pp. 30-37.

Teterycz et al, Anomalous behaviour of new thick film gas sensitive composition, 1998, Elsevier Science S.A., Sensors and Acuators B 47, pp. 153-157.

Written Opinion issued for PCT/US07/21928, dated Mar. 13, 2008.

International Search Report issued for PCT/US07/21928, dated Mar. 13, 2008.

European Search Opinion issued for European Patent Application No. 07852744, dated Apr. 23, 2012.

Supplementary European Search Report issued for European Patent Application No. 07852744, dated Apr. 23, 2012.

* cited by examiner

Step (1): Extrusion and Sintering of Support

Step (2): Deposition of Patterned Electrodes

Step (3): Deposition of Sensor Material Coating

1. Fabrication of micro-tubes

2. Deposition of Bottom Electrode

3. Deposition of Sensor Coating

4. Deposition of Top Electrode

HYDROGEN-SELECTIVE POROUS COMPOSITE

CROSS-REFERENCE TO RELATED APPLICATIONS

This application is a continuation of U.S. patent application Ser. No. 11/974,520, filed Oct. 12, 2007, issued Apr. 21, 2015 as U.S. Pat. No. 9,011,778, which claims priority from U.S. Provisional Patent Application No. 60/851,220, filed Oct. 12, 2006, the entire contents of each of which is incorporated herein by reference.

BACKGROUND

Fuel cells may be used to provide power for cars and homes, and distributed hydrogen production systems such as hydrogen filling stations may become commonplace. Safe implementation of hydrogen may be desirable for commercial acceptance of fuel cell technology. Hydrogen safety sensors may be important components of such fuel cell systems. Conventional hydrogen sensors may lack desirable: sensitivity; low cross-sensitivity to other contaminants such as carbon monoxide, hydrocarbons, and volatile organic compounds; response and recovery times, long-term stability, and the like. For chemical resistor type hydrogen sensors, desirable performance characteristics may include, for example: broad $H_2$ detection range, e.g., 1000 ppm (parts per million) to 1%; $H_2$ sensitivity, e.g., >50% resistance change at 1% $H_2$ in air; wide ambient temperature range, e.g., −40 to 200° C.; response time $t_{90}$ to 90% resistance change responsive to change in $H_2$ concentration, e.g., <30 seconds; broad humidity range, e.g., 0 to 100% RH; low cross-sensitivity, e.g., none to CO, $CH_4$, $NH_3$, humidity, VOCs, or other gases; no recalibration, e.g., stable baseline resistance and sensitivity; low power, e.g., less than 1 watt; low, e.g., 0-5 volt signals compatible with low-cost electronics; and the like.

The present application appreciates that providing capable hydrogen sensors may be a challenging endeavor.

SUMMARY

In one embodiment, a method for detecting hydrogen is provided. The method may include providing a hydrogen-comprising gas. The method may include providing a hydrogen-selective porous composite. The hydrogen-selective porous composite may include cerium oxide. The method may include contacting the hydrogen-comprising gas to the hydrogen-selective porous composite. The method may include selectively detecting hydrogen in the hydrogen-comprising gas. The hydrogen in the hydrogen-comprising gas may be selectively detected according to a decrease in an electrical resistance of the hydrogen-selective porous composite.

In another embodiment, a kit for detecting hydrogen is provided. The kit may include a hydrogen gas sensor device. The hydrogen gas sensor device may include a support. The hydrogen gas sensor device may include electrodes on a first surface of the support. The hydrogen gas sensor may include a hydrogen-selective porous composite coated on the first surface of the support. The hydrogen-selective porous composite may include cerium oxide. The hydrogen-selective porous composite may contact the electrodes such that an electrical resistance of the hydrogen-selective porous composite may be measurable at the electrodes. The kit may include instructions. The instructions may include directions to contact a hydrogen-comprising gas to the hydrogen-selective porous composite of the hydrogen gas sensor device. The instructions may include directions to selectively detect hydrogen in the hydrogen-comprising gas by measuring a decrease in the electrical resistance of the hydrogen-selective porous composite at the electrodes.

In one embodiment, a hydrogen gas sensor device is provided. The hydrogen gas sensor device may include a support. The hydrogen gas sensor device may include electrodes on a first surface of the support. The hydrogen gas sensor device may include a hydrogen-selective porous composite coated on the first surface of the support. The hydrogen-selective porous composite may contact the electrodes such that an electrical resistance of the hydrogen-selective porous composite may be measurable at the electrodes. The hydrogen-selective porous composite may include a metal oxide modifier. The metal oxide modifier may be in contact with cerium oxide. The metal oxide modifier may be present in an amount of up to about 5 wt % of the hydrogen-selective porous composite.

In another embodiment, a composition is provided. The composition may include a hydrogen-selective porous composite. The hydrogen-selective porous composite may include a metal oxide modifier. The metal oxide modifier may be in contact with cerium oxide. The metal oxide modifier may be present in an amount of up to about 5 wt % of the hydrogen-selective porous composite.

BRIEF DESCRIPTION OF THE DRAWINGS

These and further objects of the invention will become apparent from the following detailed description.

DETAILED DESCRIPTION

Figure 1:
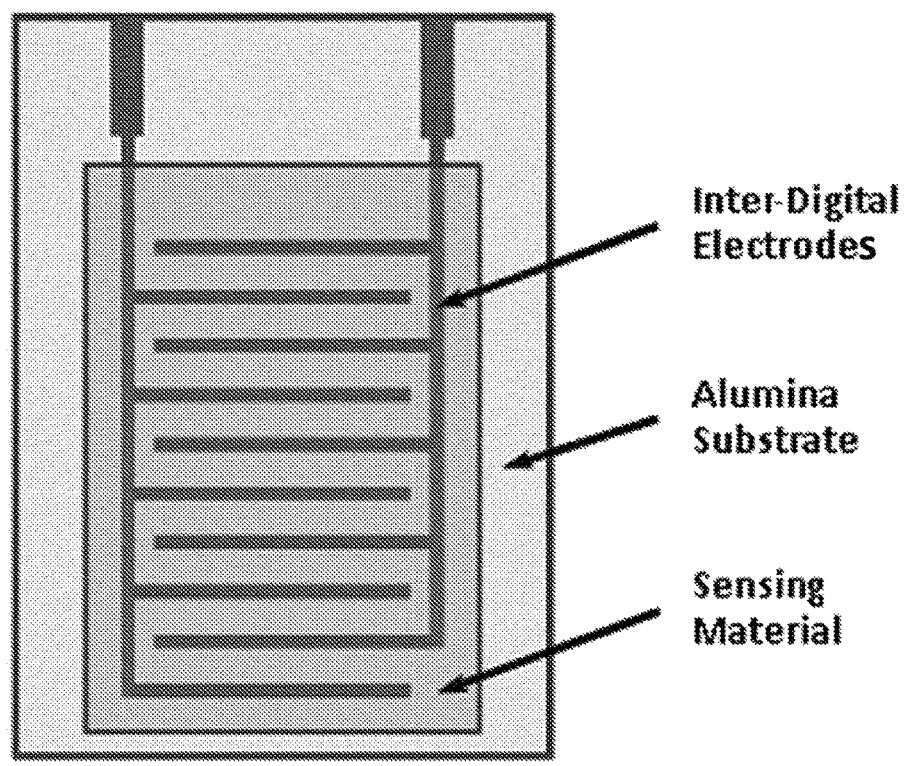
FIG. 1 is a schematic diagram of an inter-digital electrode (IDE) substrate used for planar sensor fabrication and testing.

Described are hydrogen sensitive composite materials based on cerium oxide. The hydrogen sensitivity may include a large and reversible change in the electrical resistance of a cerium oxide thick film on a heated substrate. The hydrogen sensitivity may include a large and reversible change in the electrical resistance of a cerium oxide thick film under operating conditions that may operate without a heated substrate. The cerium oxide composition may include additives to: enhance sensitivity to hydrogen, reduce cross-sensitivities to interfering gases, lower the operating temperature, and the like. The hydrogen sensitive composite materials may detect hydrogen levels ranging from approximately 500 ppm (parts per million) up to and above 1% hydrogen in air. The hydrogen sensitive composite materials may exhibit fast response and recovery times to hydrogen. The hydrogen sensitive composite materials may exhibit minimal cross sensitivity to interfering gases such as carbon monoxide and methane.

The hydrogen sensitive composite materials may include a cerium oxide based composition including, but not limited to, cerium oxide, zirconium doped ceria, gadolinium doped ceria, samarium doped ceria, lanthanum doped ceria, yttrium doped ceria, calcium doped ceria, strontium doped ceria, and mixtures thereof. The precursor to the cerium oxide based composition may contain fugitive materials to increase the porosity of the composite material.

As used herein, the term "cerium oxide based composition" includes mixtures of a cerium oxide based composition with inert materials (e.g., aluminum oxide), provided that the amount of ceria may be sufficient to achieve a desired response to the presence of hydrogen.

The hydrogen sensitive composite materials also may include a second phase modifier, a noble metal promoter, or a combination thereof. The modifier may include one or more of: tin oxide, indium oxide, titanium oxide, copper oxide, cobalt oxide, tungsten oxide, molybdenum oxide, nickel oxide, iron oxide, niobium oxide, vanadium oxide, a transition metal oxide, a mixture of transition metal oxides, solid solutions containing one or more transition metal oxide, one or more compounds each containing at least one transition metal oxide, and the like. The promoter may include palladium, ruthenium, platinum, gold, rhodium, iridium, combinations of two or more noble metals, and the like. Compositions useful for detecting hydrogen may extend over a broad range of formulations, such that the amount of the ceria-containing phase may be from 1 to 100 weight percent, the amount of the modifier phase may be from 0 to 99 percent, and the amount of the precious metal promoter may be from 0 to 99 weight percent.

The hydrogen sensitive composite materials may be incorporated into a hydrogen sensor device for use in any residential or industrial application in which hydrogen may be present. Such hydrogen sensor devices may be suitable for use in various applications including continuous area monitoring of dangerous levels of hydrogen in air. The monitoring may, for example, take place inside a housing for a fuel cell stack, reformer, or development test stand, or in more open locations such as laboratories, refueling stations, garages, and the like. Applications in which the sensor device may be used for long term monitoring may include operation of the sensor device over a wide range of environmental conditions without producing false alarms, since even sensors used in controlled indoor environments may encounter broad swings in temperature and humidity.

Two approaches may be used make a sensor that may be immune to changes in environmental conditions such as temperature and humidity. For example, compensation may be provided to adjust a signal from a sensor element affected by temperature or humidity based on external feedback. Compensation may be accomplished, for example via programmed logic in the electronics into which the sensor is integrated. Compensation may employ calibration of the environmental impact on the sensor signal, and may be subject to drift over the sensor life. In another example, a sensor element may be provided having a signal that is not affected by changes in environmental conditions and may operate without compensation.

In various embodiments, a hydrogen sensor device may include a support, electrodes applied to a surface of the support, and a sensor coating of hydrogen sensitive material applied over the electroded support. The sensor device may have a tubular or a planar geometry.

The sensor device may include an integral resistive heater. The sensor device may be used under conditions without an integral heater, for example, if the sensor material works at room temperature or the gas to be sensed is at an elevated temperature. If such a heater is used, the heater resistance may be selected to minimize the sensitivity of the hydrogen sensitive material to variations in relative humidity. The operating temperature may be selected to control the cross-sensitivity of the sensor device to gases other than hydrogen. Furthermore, the resistance and resulting current of the heater may be selected to minimize unwanted sensitivity of the sensor to variations in relative humidity. The sensor device may also effectively detect certain other gases even when no heater is present if the sensor materials for that gas perform appropriately at the ambient temperature, the stream of gas to be analyzed is at an elevated temperature, or the sensor device may be used in a tube oven or similar environment.

The support may be made from one or more of: aluminum oxide, yttria stabilized zirconia, cerium oxide, gadolinium doped ceria, magnesium aluminate, magnesium oxide, or any other ceramic material with sufficiently low electrical conductivity for sensor applications. Other support material compositions may be used, depending on the gas sensing application, the sensor coating material, and the operating temperature. The support and the sensor coating may be formed from essentially the same material to eliminate thermal expansion mismatches. For example, the support for the hydrogen sensor may be made from aluminum oxide ($Al_2O_3$) or magnesium oxide (MgO), which may have advantages with respect to higher mechanical strength and thermal conductivity.

The electrodes applied to the support may be gold, silver, platinum, or any suitable metal. An inter-digital electrode pattern may be used as described. Any electrode geometry may work as long as the resistance of the sensor material coating may be in the desired range within a corresponding operational temperature range.

One embodiment of the hydrogen sensor device may include a planar ceramic support, electrodes applied to a surface of the support, and a coating of the above-described hydrogen sensitive composite material applied to the electroded surface. A resistive heater may be printed on or bonded to the opposite side of the support, or contained within the support itself.

Another embodiment of the hydrogen sensor device may include a ceramic micro-tubular support, electrodes applied to the outer surface of the support, and a coating of the above-described hydrogen sensitive composite material applied onto the electroded outer surface of the support. The tubular support may provide an increased surface to volume ratio. The support tube may have an outer diameter of 0.5 to 5 mm (millimeters) and a wall thickness of 100 to 1000 microns. When a resistive heater is used, the heater wire described further below may be inserted into the interior of the ceramic micro-tube and bonded at the tube ends. Essentially all of the heat may be applied to the tubular sensor when current is applied to the heater wire rather than lost to the environment, which may greatly reduce heating power compared to a planar support.

In some embodiments, a gas sensor device with improved baseline resistance to the adverse effects of an environmental condition is provided. The gas sensor device may include a support, electrodes applied to the support, and a dual sensor element. The dual sensor may include two different sensor coating materials selected to cancel unwanted environmental effects, such as ambient temperature variation. Each of the sensors may be located on a separate support, optionally with separate heaters, or both sensors may be located on a single support. A dual sensor element may be included in the above-described hydrogen sensor device.

The hydrogen-sensitive composite sensor materials were developed and demonstrated using a prior art planar device platform shown in FIG. 1. The planar device included coatings of sensor materials deposited onto a ceramic substrate, aluminum oxide, with inter-digital electrodes (IDEs). Lead wires were attached to provide measurement of a resistance proportional to the electrical resistivity of the sensor material. The planar device may be placed in a tube furnace to determine the resistive responses of the sensor material coating to hydrogen or other gases of interest at different temperatures. Alternatively, a heater may be printed on or bonded to the opposite face of the planar device to heat the substrate to the desired operating temperature without a furnace.

Figure 12:
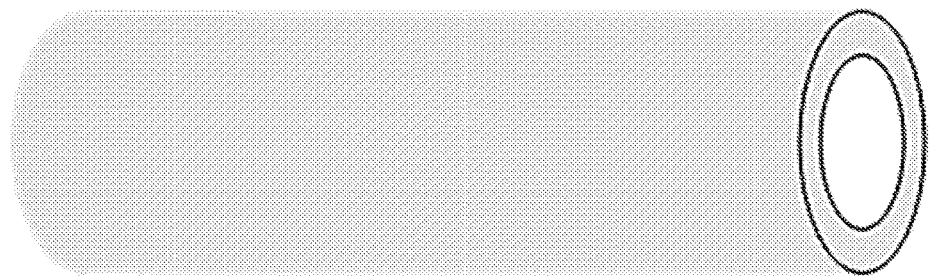
FIG. 12 is a schematic diagram showing manufacturing steps used to produce the micro-tubular sensors of EXAMPLE 20.
Figure 12:
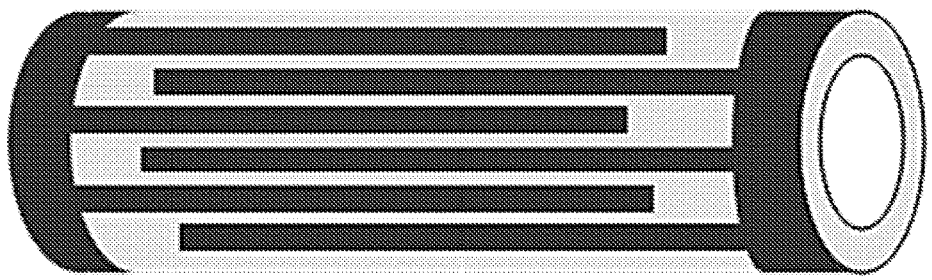
Figure 12:
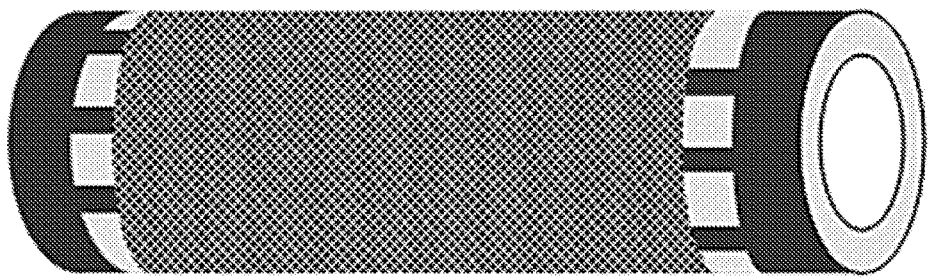
Figure 31:
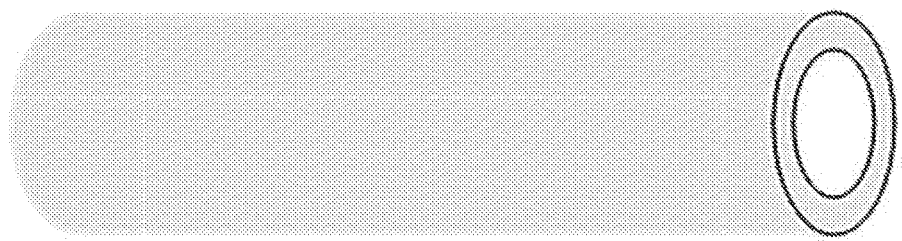
FIG. 31 is a schematic diagram showing the manufacturing steps used to produce exemplary micro-tubular sensors.
Figure 31:
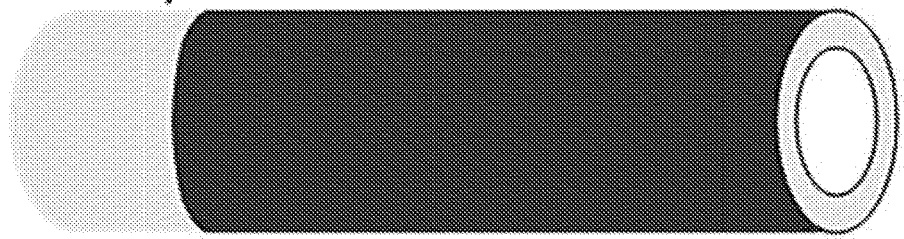
Figure 31:
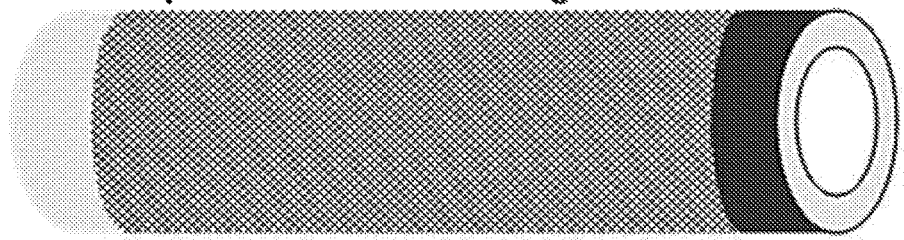
Figure 31:
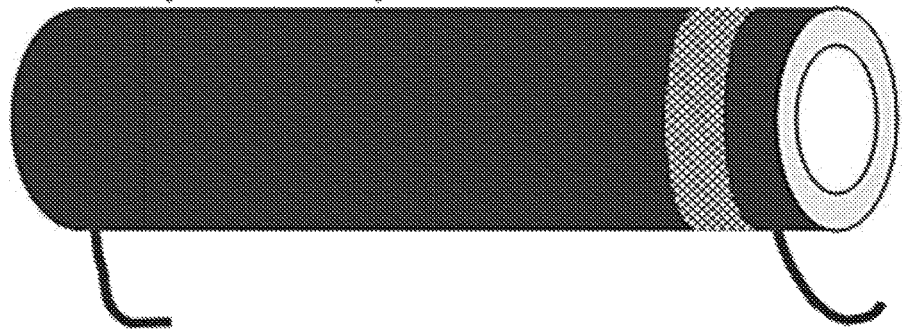
Figure 32:
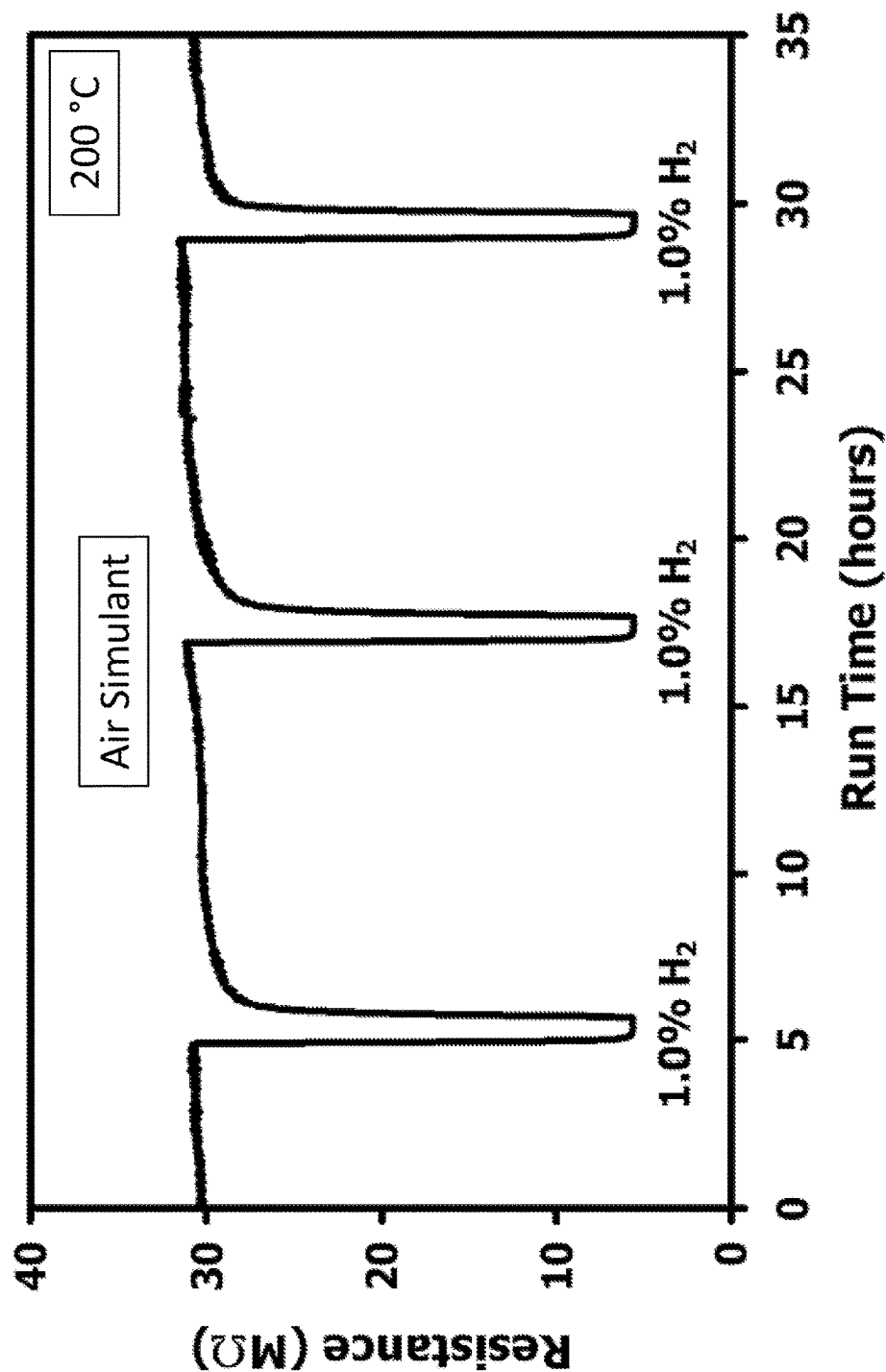
FIG. 32 is a graph showing the sensitivity of a micro-tubular $H_2$ sensor prepared using the manufacturing steps shown in FIG. 31.

Electrodes were applied to the outer surface of the tubular support and a coating of a sensor material was applied over the electroded surface. The sensor device may be prepared as shown in FIG. 12 by applying electrodes in a pattern to the outer surface of the tubular support and then applying a coating of a sensor material over the electroded surface. Alternatively, the sensor may be produced as shown in FIG. 31 by applying an electrode material to a portion of the tubular support adjacent to a first end of the support but not covering the portion adjacent to the second end of the support; applying a coating of a sensor material offset from the electrode layer such that a portion of the electrode layer nearest the first end remains exposed and the remainder of the electrode layer and a portion of the uncovered tubular support adjacent to the second end are covered by the sensor material coating; and applying a second layer of an electrode material offset from the sensor material coating such that a portion of the sensor material coating nearest the first end remains exposed and the remainder of the sensor material coating and the uncoated portion of the tubular support are covered by the second electrode layer. Data obtained on a device fabricated in this fashion are shown in FIG. 32.

Sensor devices were tested using a digital multimeter connected via serial port to a computer for controlled data acquisition. The sensor test stands had fully automated data collection and process control through integration with software (LABVIEW™ software, National Instruments, Austin, Tex.). A programmable tube furnace, housed in a leak-tight quartz tube with wire feedthroughs for electrical measurements, was used to control the temperature of the sensor.

The simulated gas mixtures were produced from three standard compressed gas cylinders: one that contained 2% $H_2$ in nitrogen, a second that contained pure nitrogen, and a third that contained a mixture of oxygen and nitrogen. Digital mass flow controllers were used to control the gas composition within the sensor chamber.

Provided are materials that may be extremely sensitive to hydrogen. Also provided is a hydrogen sensor device including the hydrogen sensitive material. The hydrogen sensor device may be sensitive to $H_2$ in air. The hydrogen sensor device may provide quantifiable resistive responses within a desired range of 1000 ppm to 1 percent $H_2$. The hydrogen sensor device may not exhibit cross-sensitivities to interfering gases such as CO and $CH_4$. The hydrogen sensor device may exhibit rapid response and recovery times. The hydrogen sensor device may be capable of operating over a wide temperature range. The hydrogen sensor device may exhibit stable performance over long time periods. The hydrogen sensor device may have low power usage. The hydrogen sensor device may be easy to manufacture at low cost. Also provided is a tubular sensor device useful for chemical resistor type gas sensor materials. The sensor device may include a heater configuration to minimize sensitivity of the sensor to variations in relative humidity. The sensor device may include a dual sensor to cancel undesirable effects on a baseline resistance, for example, undesirable effects resulting from atmospheric temperature changes.

In various embodiments, a hydrogen sensitive composite material is provided. The hydrogen sensitive composite material may include a cerium oxide composition. The cerium oxide composition may include one or more of: cerium oxide, zirconium doped ceria, gadolinium doped ceria, samarium doped ceria, lanthanum doped ceria, yttrium doped ceria, calcium doped ceria, strontium doped ceria, and mixtures thereof. The hydrogen sensitive composite material may include a modifier including one or more of: tin oxide, indium oxide, titanium oxide, copper oxide, cobalt oxide, tungsten oxide, molybdenum oxide, nickel oxide, iron oxide, niobium oxide, vanadium oxide, a transition metal oxide, a mixture of transition metal oxides, a solid solution containing at least one transition metal oxide, a compound containing at least one transition metal oxide, and a mixture of at least two compounds each containing at least one transition metal oxide. The hydrogen sensitive composite material may include a noble metal promoter including one or more of: palladium, ruthenium, platinum, gold, rhodium, iridium, and a combination thereof. The hydrogen sensitive composite material may include both a modifier and a promoter. The hydrogen sensitive composite material may include 1-100 wt % of a cerium oxide composition, 0-99 wt % of a modifier, and 0-99 wt % of a noble metal promoter.

In some embodiments, a hydrogen gas sensor device is provided. The hydrogen gas sensor device may include a support, electrodes applied to a surface of the support, and a sensor coating applied to the electroded surface of the support. The sensor coating may include the hydrogen sensitive composite material. The support may be formed from a material including one or more of: aluminum oxide, yttria stabilized zirconia, cerium oxide, gadolinium doped ceria, magnesium aluminate, and magnesium oxide.

In several embodiments, the hydrogen gas sensor device may include an integral resistive heater. The hydrogen gas sensor device may be characterized by an operating temperature selected to control the cross-sensitivity of the sensor device to gases other than hydrogen. The heater may be characterized by a resistance selected to control sensitivity of the sensor device to relative humidity. The support may include a micro-tubular support. The resistive heater may be inserted into the interior of the micro-tubular support. The resistive heater may be bonded at tube ends of the micro-tubular support. Alternatively, the support may be planar and the resistive heater may be applied to the support surface opposite the electroded surface.

In various embodiments, a gas sensor device is provided. The gas sensor device may include a support, electrodes applied to a surface of the support, and a dual sensor element in electrical communication with the electrodes. The dual sensor element may include a first sensor including an unpromoted composite material that may be relatively insensitive to the target gas, a second sensor including a promoted composite material that may be sensitive to the target gas, and an apparatus for comparing a measurement obtained from the first sensor element and a measurement obtained from the second sensor element. The comparison so obtained may be used to compensate for the adverse effect of an environmental condition on the baseline resistance of the gas sensor device. The first and second sensor elements may be located on the same support. The support may be a micro-tubular support. A resistive heater may be included within the micro-tubular support. The resistive heater may be bonded at tube ends of the micro-tubular support. The operating temperature of the gas sensor device including a resistive heater may be selected to control the cross-sensitivity of the sensor device to gases other than the target gas. The heater may be characterized by a resistance selected to control sensitivity of the sensor device to relative humidity. The dual sensor element may be selected to compensate for the adverse effect of an environmental condition other than relative humidity on the baseline resistance of the gas sensor device. The gas sensitive composite material may be the hydrogen sensitive composite material described herein, e.g., a cerium oxide composition.

EXAMPLES

The following examples illustrate the processes and compositions of described herein for hydrogen sensitive material formulations based on cerium oxide. The following examples are merely illustrative and should not be construed to limit the scope of the embodiments described herein in any way.

Example 1: $H_2$ Sensors Based Solely on Cerium Oxide

Figure 2:
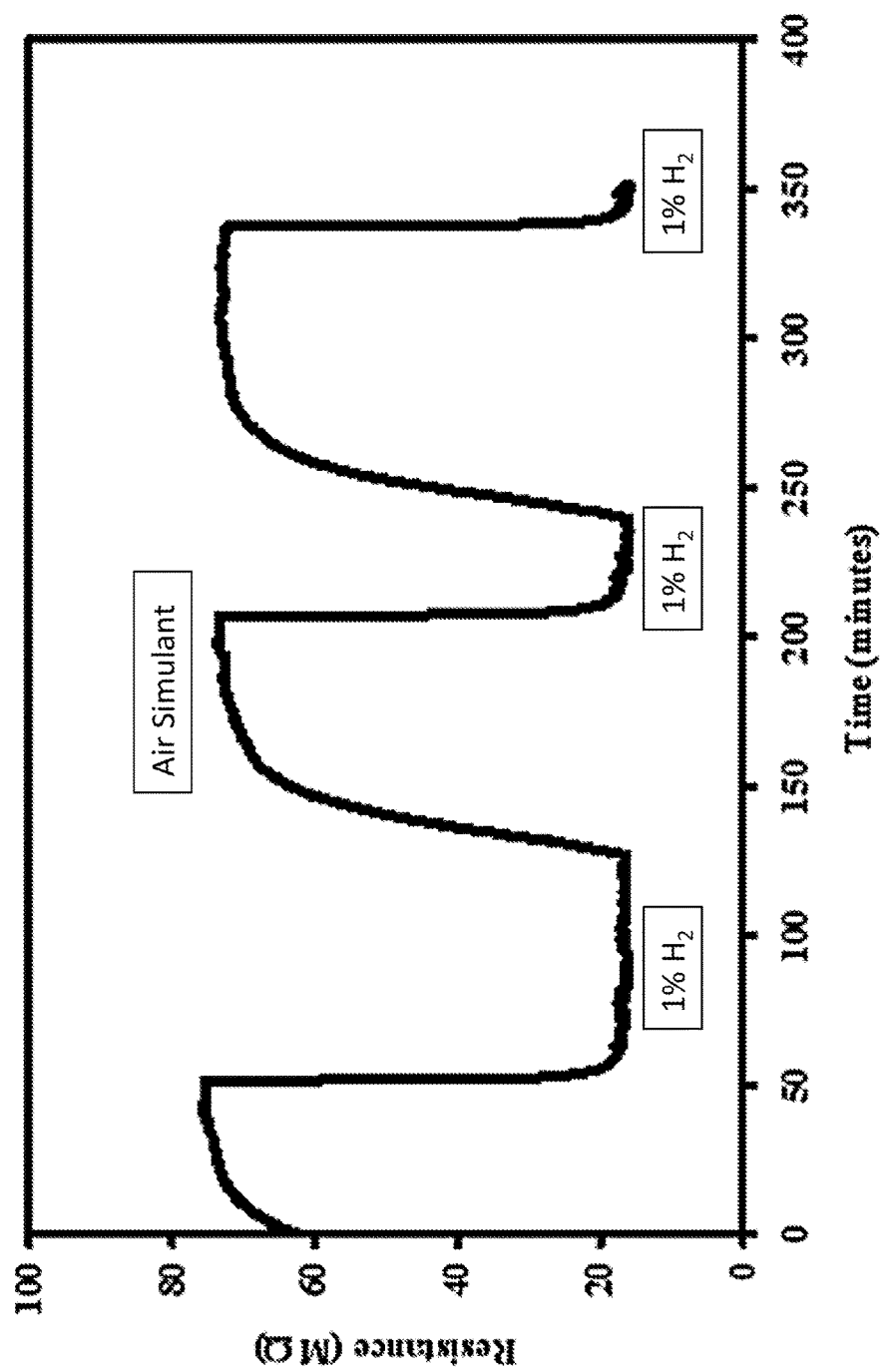
FIG. 2 is a graph of $H_2$ sensitivity for the $CeO_2$ sensor of EXAMPLE 1, showing repeatable responses to 1% $H_2$ at 400° C.
Figure 3:
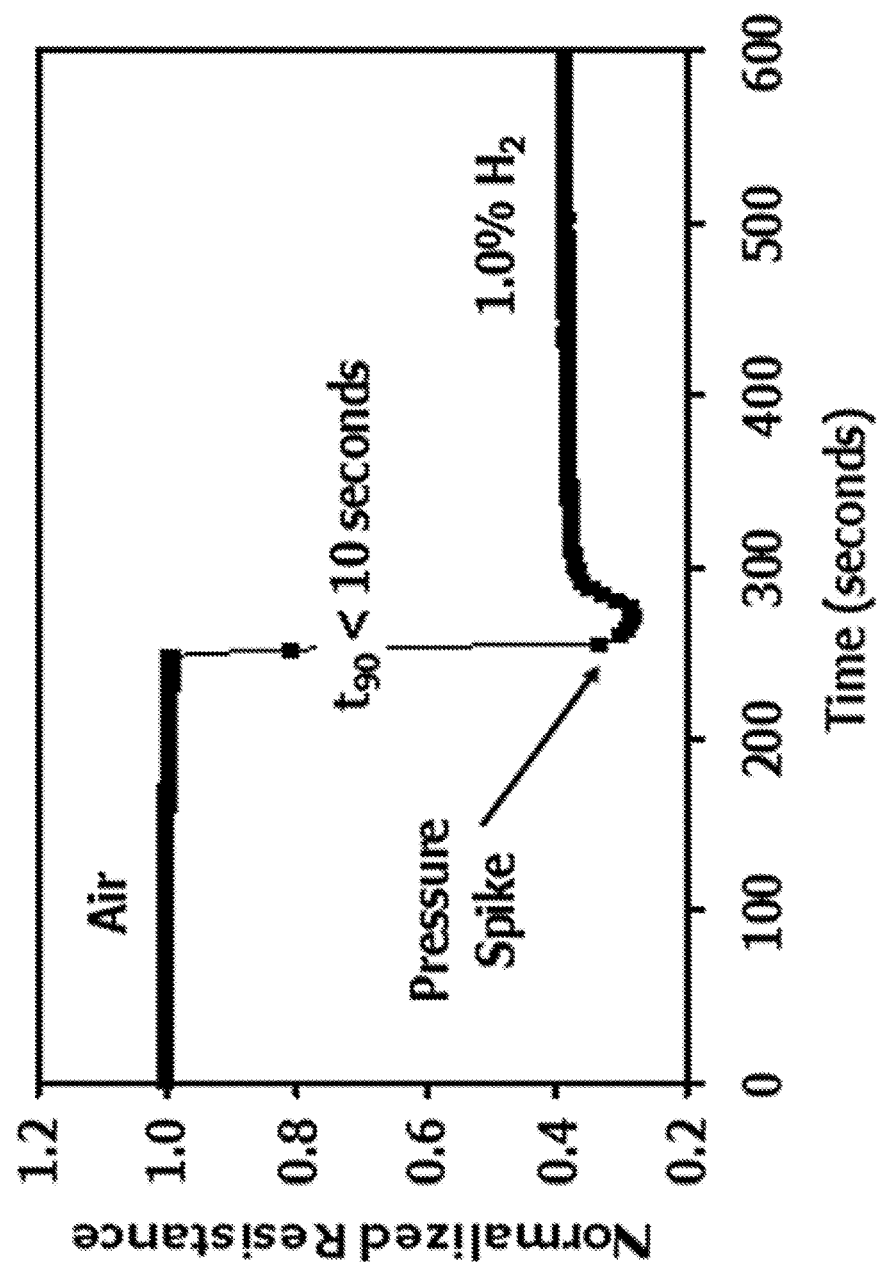
FIG. 3 is a graph of the response of the $CeO_2$ sensor of EXAMPLE 1 to 1% $H_2$ in air at 400° C.

An ink was prepared by mixing 14 $m^2$/g surface area $CeO_2$ powder with vehicle (Johnson Matthey 63/2 Medium, Johnson Matthey, San Jose, Calif.) in a 2:1 ratio of powder to vehicle using a mortar and pestle. The ink was painted on the surface of a 5-mm×5-mm aluminum oxide substrate with inter-digital electrodes and then annealed at 800° C. for one hour. The sensor was tested as described above at various temperatures. Maximum hydrogen sensitivity was obtained at a temperature of 400° C. As shown in FIG. 2, the planar device with a sensor coating material based solely on $CeO_2$ provides a large and repeatable response to 1% hydrogen. When 1% $H_2$ was introduced, the device resistance was reduced from about 75 MΩ to about 18 MΩ, which corresponds to a sensitivity of about 75 percent. When $H_2$ was removed, the device resistance returned to its original level. As shown in FIG. 3, the response of this sensor to hydrogen was extremely rapid, taking less than about ten seconds to achieve 90% of its resistance change after 1% $H_2$ was introduced. While the sensor material based solely on $CeO_2$ exhibited very high sensitivity to hydrogen, a high operating temperature was used to achieve maximum sensitivity, probably because resistance was extremely high at lower temperatures. Operation of the sensor at such high temperatures used relatively high heater power for the sensor.

Example 2: $H_2$ Sensors Based on Gadolinium Doped Ceria

Figure 4:
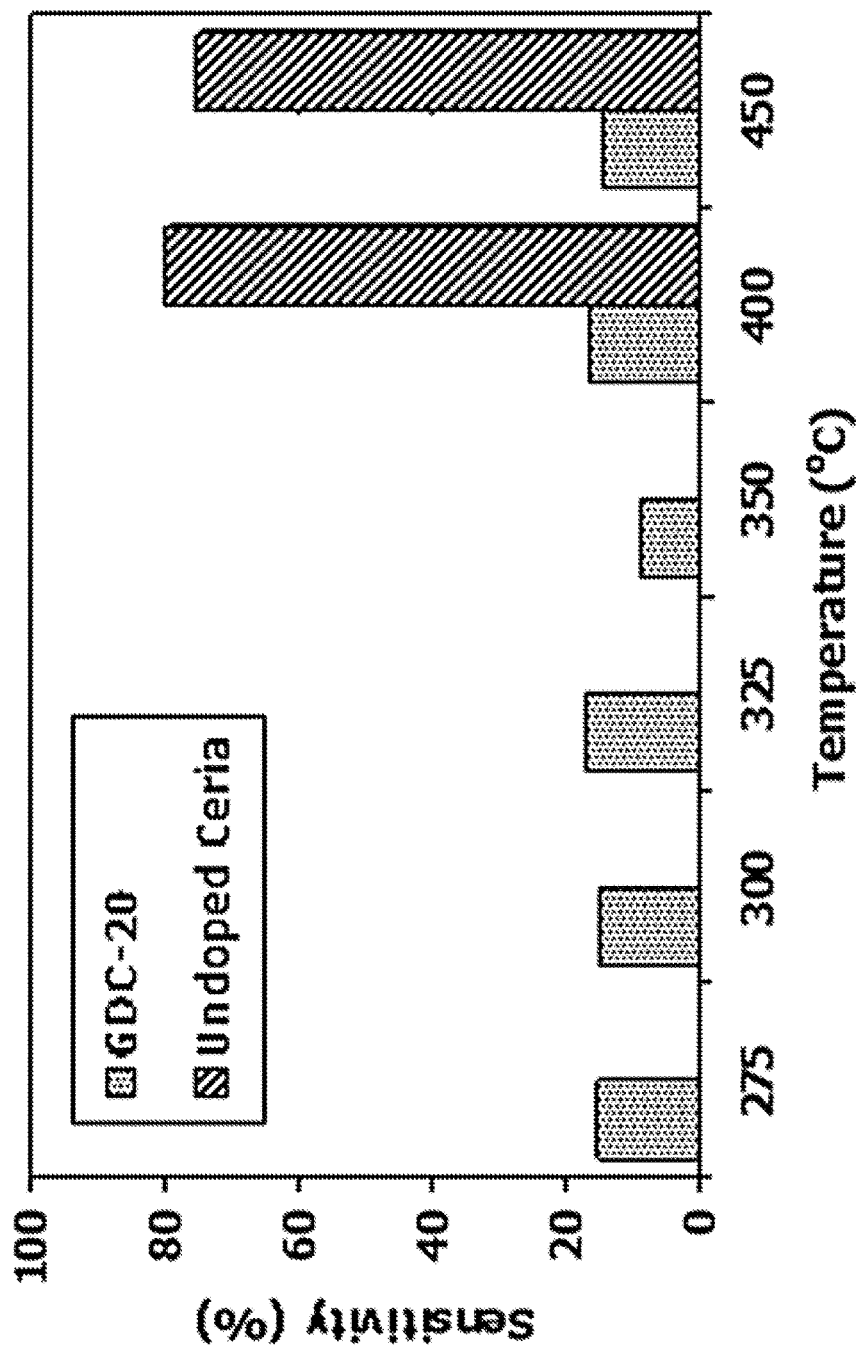
FIG. 4 is a graph of $H_2$ sensitivity versus temperature for the $CeO_2$ and GDC sensors of EXAMPLES 1 and 2, respectively.

To reduce the operating temperature, 20 mol % of gadolinium was substituted in the crystal structure of $CeO_2$, creating oxygen vacancies in the structure and increasing ionic conductivity at lower temperatures. This ceria based electrolyte composition (GDC) is well known in the field of solid state ionics, although the sensitivity of the composition to hydrogen levels present in fuel cell applications was not known. The GDC sensor was made as described in EXAMPLE 1. An ink was prepared by mixing 12 $m^2/g$ surface area GDC powder with Johnson Matthey 63/2 Medium vehicle in a 2:1 ratio of powder to vehicle using a mortar and pestle. The ink was painted on the surface of a 5-mm×5-mm aluminum oxide substrate with inter-digital electrodes and then annealed at 800° C. for one hour. The sensor was tested as described above at various temperatures. Hydrogen sensitivity was obtained over a wide temperature range. The data in FIG. 4, which compare the hydrogen sensitivities (percent change of resistance after exposure to 1% $H_2$) of the $CeO_2$ sensor of EXAMPLE 1 with the GDC sensor of EXAMPLE 2, demonstrate that the GDC sensor retained sensitivity to hydrogen at temperatures as low as 275° C. The magnitude of hydrogen sensitivity was lower for the GDC sensor compared to the $CeO_2$ sensor.

Examples 3, 4, 5, and 6: $CeO_2$ Based Sensors with Second Phase Additions of $SnO_2$ or $In_2O_3$ The effects of second phase additions of $In_2O_3$ or $SnO_2$ on hydrogen sensitivity of $CeO_2$ based sensors were evaluated. Multiple composite inks were prepared using methods described above for EXAMPLES 1 and 2. High surface area $SnO_2$ and $In_2O_3$ powders were added to $CeO_2$ powder at 2.5 and 5 wt % levels. Planar sensors were fabricated and tested, also using previously described methods. Hydrogen sensitivities were measured at different temperatures, with data presented in TABLE 1.

TABLE 1

Sensitivities of $CeO_2$ based sensors to 1% $H_2$ in dry simulated air at different temperatures.

| Ex. | Formulation | 400° C. | 415° C. | 425° C. | 430° C. | 450° C. | 500° C. | 550° C. | 575° C. | 600° C. |
|---|---|---|---|---|---|---|---|---|---|---|
| 1 | $CeO_2$ | 80.0% | | | | 75.3% | | | | |
| 3 | $CeO_2$ (2.5 wt % $SnO_2$) | | | | 72.5% | 72.9% | 61.1% | 49.0% | | 41.8% |
| 4 | $CeO_2$ (5.0 wt % $SnO_2$) | | 76.1% | | | 67.6% | 58.1% | 32.3% | | 22.0% |
| 5 | $CeO_2$ (2.5 wt % $In_2O_3$) | | | 51.2% | | 48.5% | 32.2% | 24.2% | | 28.0% |
| 6 | $CeO_2$ (5.0 wt % $In_2O_3$) | | | 46.3% | | 51.4% | 38.9% | 36.4% | | 28.7% |

The interference resistance, or cross-sensitivity, for each sensor was also evaluated by testing the response of the sensors to 200 ppm CO and to 0.5 vol % $CH_4$. The 200 ppm CO level was selected as corresponding to the evacuation level for industrial facilities. The 0.5 vol % $CH_4$ level was selected as corresponding to 10% of the lower explosive limit of methane. Comparisons were made by determining the "relative sensitivity" to hydrogen using the following equation:

Relative Sensitivity=(Sensitivity to 1% $H_2$)−(Cross-sensitivity)

If a sensor has no cross-sensitivity to CO, the relative sensitivity equals the sensitivity for that sensor. A negative relative sensitivity means that the sensor is more sensitive to the interference gas than to hydrogen. The relative sensitivities measured for $CeO_2$ based sensors are provided in TABLES 2 and 3.

TABLE 2

Relative sensitivities of $CeO_2$ sensors to 1% $H_2$ in simulated air with 200 ppm CO vs temperature.

| Ex. | Formulation | 400° C. | 415° C. | 425° C. | 430° C. | 450° C. | 500° C. | 550° C. | 575° C. | 600° C. |
|---|---|---|---|---|---|---|---|---|---|---|
| 1 | $CeO_2$ | 59.6% | | | | | | | | |
| 3 | $CeO_2$ (2.5 wt % $SnO_2$) | | | | 36.0% | 49.1% | 51.4% | 43.2% | 39.7% | |
| 4 | $CeO_2$ (5.0 wt % $SnO_2$) | | 36.2% | | | 47.3% | 46.9% | 25.0% | | 17.8% |
| 5 | $CeO_2$ (2.5 wt % $In_2O_3$) | | | 25.8% | | 31.4% | 23.6% | 15.3% | | 27.5% |
| 6 | $CeO_2$ (5.0 wt % $In_2O_3$) | | | 22.3% | | 36.8% | 32.4% | 34.5% | | 27.5% |

TABLE 3

Relative sensitivities of $CeO_2$ sensors to 1% $H_2$ in simulated air with and 0.5 vol % of $CH_4$ vs temperature.

| Ex. | Formulation | 400° C. | 415° C. | 425° C. | 430° C. | 450° C. | 500° C. | 550° C. | 575° C. | 600° C. |
|---|---|---|---|---|---|---|---|---|---|---|
| 1 | $CeO_2$ | | | | | | | | | |
| 3 | $CeO_2$ (2.5 wt % $SnO_2$) | | | | 51.1% | 53.9% | 51.5% | 39.2% | 35.7% | |
| 4 | $CeO_2$ (5.0 wt % $SnO_2$) | | 62.8% | | | 49.9% | 12.3% | −6.9% | | −6.5% |
| 5 | $CeO_2$ (2.5 wt % $In_2O_3$) | | | 15.6% | | 21.0% | 20.0% | 15.9% | | 20.7% |
| 6 | $CeO_2$ (5.0 wt % $In_2O_3$) | | | 24.0% | | 30.9% | 20.6% | 2.00% | | 1.80% |

Examples 7, 8, 9, and 10: GDC Based Sensors with Second Phase Additions of $SnO_2$ or $In_2O_3$ The effects of second phase additions of $In_2O_3$ or $SnO_2$ on hydrogen sensitivity of GDC based sensors also were evaluated. Multiple composite inks were prepared using methods described above. High surface area $SnO_2$ and $In_2O_3$ powders were added to GDC powder at 2.5 and 5 wt % levels. Planar sensors were fabricated and tested, also using previously described methods. Hydrogen sensitivities and relative sensitivities were measured at different temperatures, with data presented in TABLES 4 and 5, respectively.

TABLE 4

Sensitivities of GDC sensors to 1% $H_2$ in dry simulated air vs temperature.

| Ex. | Formulation | 225° C. | 230° C. | 250° C. | 275° C. | 300° C. | 325° C. | 350° C. | 400° C. | 450° C. |
|---|---|---|---|---|---|---|---|---|---|---|
| 1 | GDC | | 21.1% | | 15.2% | 14.8% | 17.0% | 8.70% | 16.2% | 14.4% |
| 7 | GDC (2.5 wt % $SnO_2$) | 20.8% | | 7.92% | | 12.5% | | 8.80% | | 27.9% |
| 8 | GDC (5.0 wt % $SnO_2$) | | | 14.0% | | 7.20% | | 23.5% | 8.35% | |
| 9 | GDC (2.5 wt % $In_2O_3$) | 16.8% | | 7.49% | | 19.4% | | 6.23% | | |
| 10 | GDC (5.0 wt % $In_2O_3$) | | | 4.86% | | 7.63% | | 21.4% | 6.30% | 7.32% |

TABLE 5

Relative Sensitivities of GDC sensors to 1% $H_2$ in simulated air with CO and $CH_4$ vs temperature.

| | | 200 ppm CO | | | | 0.5 vol % $CH_4$ | | | |
|---|---|---|---|---|---|---|---|---|---|
| Ex. | Formulation | 250° C. | 300° C. | 350° C. | 400° C. | 250° C. | 300° C. | 350° C. | 400° C. |
| 1 | GDC | | | | | | | | |
| 7 | GDC (2.5 wt % $SnO_2$) | 7.00% | 11.3% | | 30.5% | 7.30% | 12.0% | | 31.0% |
| 8 | GDC (5.0 wt % $SnO_2$) | 7.10% | 4.40% | 15.3% | 7.60% | 10.6% | 4.60% | 22.0% | 7.93% |
| 9 | GDC (2.5 wt % $In_2O_3$) | 10.6% | 16.9% | 6.6% | | 11.8% | 21.2% | 9.20% | |
| 10 | GDC (5.0 wt % $In_2O_3$) | | 5.43% | 14.8% | 6.80% | 11.2% | 12.7% | 23.2% | 8.70% |

Figure 5:
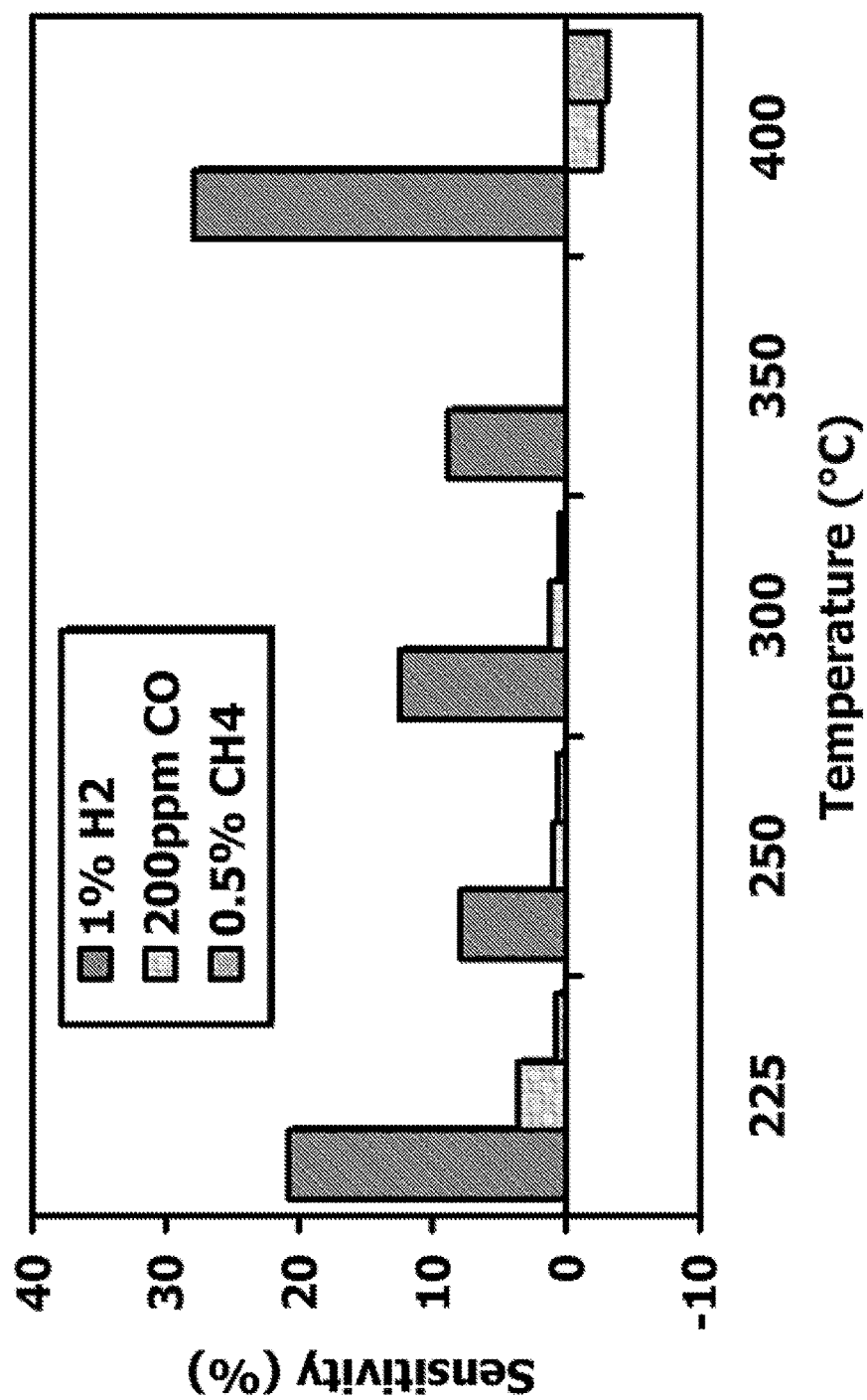
FIG. 5 is a graph of resistive responses of the GDC (2.5% $SnO_2$) sensor of EXAMPLE 7 to $H_2$, CO, and $CH_4$ at various temperatures, showing zero cross-sensitivity at 350° C.

During the above described testing, it was unexpectedly discovered that the operating temperature of the sensor could be used to tune-out the cross-sensitivities to CO and $CH_4$. For several samples, it was noted that cross-sensitivity to both CO and $CH_4$ changed from an n-type response (decreased resistance) to a p-type response (increased resistance) at a certain temperature. This phenomenon makes it possible to engineer sensors to be immune to interference gases. The GDC (2.5% $SnO_2$) sensor of EXAMPLE 7 showed no response to either CO or $CH_4$ at 350° C., as shown in FIG. 5.

Examples 11, 12, 13 and 14: Composite $CeO_2$ Sensors with Pd and Ru Promoters $CeO_2$ based composite sensor formulations with 5-wt % second phase additions of $SnO_2$ or $In_2O_3$ were subjected to studies aimed at optimizing sensitivity through additions of a noble metal promoter. Ruthenium and palladium each was evaluated at 1-wt % levels. Palladium (II) 2,4-pentanedionate and ruthenium (III) 2,4-pentanedionate were dissolved in the Johnson Matthey vehicle and the sensor inks were prepared using the same procedure described herein. Planar sensors were fabricated and tested at different temperatures, also using methods described herein. Hydrogen sensitivity data for these $CeO_2$ based sensors are presented in TABLE 6, and relative sensitivity data are presented in TABLES 7 and 8. Palladium addition increased sensitivity to hydrogen for the $CeO_2$ based sensors. However, palladium addition increased cross-sensitivities to CO and $CH_4$ for $CeO_2$ (5% $SnO_2$) sensors, which led to lower relative sensitivities. Palladium had a slightly positive effect on the relative sensitivities of the $CeO_2$ (5% $In_2O_3$) sensors. Ruthenium addition had little effect on hydrogen sensitivity and relative sensitivities of the $CeO_2$ based sensors.

TABLE 6

Sensitivities of Pd and Ru promoted $CeO_2$ sensors to 1% $H_2$ in simulated air vs temperature.

| Ex. | Formulation | Promoter | 450° C. | 475° C. | 500° C. | 550° C. | 600° C. | 650° C. |
|---|---|---|---|---|---|---|---|---|
| 4 | $CeO_2$ (5.0 wt % $SnO_2$) | none | 67.6% | | 58.1% | 32.3% | 22.0% | |
| 11 | $CeO_2$ (5.0 wt % $SnO_2$) | 1 wt % Pd | 95.0% | | 92.3% | 88.1% | 67.4% | |
| 12 | $CeO_2$ (5.0 wt % $SnO_2$) | 1 wt % Ru | 80.3% | | 72.8% | 51.7% | 31.9% | |
| 6 | $CeO_2$ (5.0 wt % $In_2O_3$) | none | 51.4% | | 38.9% | 36.4% | 28.7% | |
| 13 | $CeO_2$ (5.0 wt % $In_2O_3$) | 1 wt % Pd | | 93.8% | 94.7% | 91.7% | 70.8% | 26.8% |
| 14 | $CeO_2$ (5.0 wt % $In_2O_3$) | 1 wt % Ru | 65.2% | | 59.6% | 45.7% | 25.2% | 17.2% |

TABLE 7

Relative sensitivities of Pd and Ru promoted CeO₂ sensors to 1% H₂ in simulated air with 200 ppm CO vs temperature.

| Ex. | Formulation | Promoter | 450° C. | 475° C. | 500° C. | 550° C. | 600° C. | 650° C. |
|---|---|---|---|---|---|---|---|---|
| 4 | CeO₂ (5.0 wt % SnO₂) | none | 47.3% | | 46.9% | 25.0% | 17.8% | |
| 11 | CeO₂ (5.0 wt % SnO₂) | 1 wt % Pd | 30.5% | | 26.9% | 42.2% | 45.6% | |
| 12 | CeO₂ (5.0 wt % SnO₂) | 1 wt % Ru | 48.3% | | 54.3% | 43.8% | 28.6% | |
| 6 | CeO₂ (5.0 wt % In₂O₃) | none | 36.8% | | 32.4% | 34.5% | 27.5% | |
| 13 | CeO₂ (5.0 wt % In₂O₃) | 1 wt % Pd | | 41.8% | 44.5% | 40.0% | 41.3% | 17.6% |
| 14 | CeO₂ (5.0 wt % In₂O₃) | 1 wt % Ru | 47.4% | | 46.7% | 42.3% | 23.3% | 16.8% |

TABLE 8

Relative sensitivities of Pd and Ru promoted CeO₂ sensors to 1% H₂ in simulated air with 0.5 vol % CH₄ vs temperature.

| Ex. | Formulation | Promoter | 450° C. | 475° C. | 500° C. | 550° C. | 600° C. | 650° C. |
|---|---|---|---|---|---|---|---|---|
| 4 | CeO₂ (5.0 wt % SnO₂) | none | 49.9% | | 12.3% | −6.90% | −6.50% | |
| 11 | CeO₂ (5.0 wt % SnO₂) | 1 wt % Pd | 42.7% | | 42.3% | 39.5% | 5.10% | |
| 12 | CeO₂ (5.0 wt % SnO₂) | 1 wt % Ru | 47.8% | | 49.8% | 16.3% | −9.30% | |
| 6 | CeO₂ (5.0 wt % In₂O₃) | none | 30.9% | | 20.6% | 2.00% | 1.80% | |
| 13 | CeO₂ (5.0 wt % In₂O₃) | 1 wt % Pd | | 32.7% | 19.8% | 23.6% | 1.80% | 30.1% |
| 14 | CeO₂ (5.0 wt % In₂O₃) | 1 wt % Ru | 25.1% | | 32.3% | 8.80% | −8.30% | −5.00% |

Examples 15, 16, 17 and 18: Composite GDC Sensors with Pd and Ru Promoters

GDC based composite sensor formulations with 5-wt % second phase additions of SnO₂ or In₂O₃ were studied to optimize sensitivity through addition of a noble metal promoter. Ruthenium and palladium each was evaluated at 1-wt % levels. Palladium (II) 2,4-pentanedionate and ruthenium (III) 2,4-pentanedionate were dissolved in the Johnson Matthey vehicle and the sensor inks were prepared using the same procedures described herein. Planar sensors were fabricated and tested at different temperatures, also using methods described herein. Hydrogen sensitivity data for these GDC sensors are presented in TABLE 9 and relative sensitivity data are presented in TABLES 10 and 11.

TABLE 9

Sensitivities of Pd and Ru promoted GDC sensors to 1% H₂ in simulated air vs temperature.

| Ex. | Formulation | Promoter | 250° C. | 275° C. | 300° C. | 350° C. | 400° C. | 450° C. |
|---|---|---|---|---|---|---|---|---|
| 8 | GDC (5.0 wt % SnO₂) | None | 14.0% | | 7.20% | 23.5% | 8.40% | |
| 15 | GDC (5.0 wt % SnO₂) | 1 wt % Pd | 45.6% | | 50.7% | 44.6% | 24.3% | 24.2% |
| 16 | GDC (5.0 wt % SnO₂) | 1 wt % Ru | 19.8% | | 19.1% | 11.8% | 20.1% | |
| 10 | GDC (5.0 wt % In₂O₃) | None | 4.86% | | 7.63% | 21.4% | 6.30% | 7.32% |
| 17 | GDC (5.0 wt % In₂O₃) | 1 wt % Pd | | 40.3% | 42.3% | 32.8% | 28.0% | 26.5% |
| 18 | GDC (5.0 wt % In₂O₃) | 1 wt % Ru | | 19.3% | 17.0% | 12.0% | 20.8% | |

TABLE 10

Relative sensitivities of Pd and Ru promoted GDC sensors to 1% H₂ in simulated air with 200 ppm CO vs temperature.

| Ex. | Formulation | Promoter | 250° C. | 275° C. | 300° C. | 350° C. | 400° C. | 450° C. |
|---|---|---|---|---|---|---|---|---|
| 8 | GDC (5.0 wt % SnO₂) | None | 7.10% | | 4.40% | 15.3% | 7.60% | |
| 15 | GDC (5.0 wt % SnO₂) | 1 wt % Pd | 43.3% | | 46.2% | 42.0% | 25.8% | 26.2% |
| 16 | GDC (5.0 wt % SnO₂) | 1 wt % Ru | 13.8% | | 16.8% | 11.5% | 18.7% | |
| 10 | GDC (5.0 wt % In₂O₃) | None | | | 5.43% | 14.8% | 6.80% | 6.69% |
| 17 | GDC (5.0 wt % In₂O₃) | 1 wt % Pd | | 42.8% | 44.2% | 34.6% | 30.1% | 29.6% |
| 18 | GDC (5.0 wt % In₂O₃) | 1 wt % Ru | | 22.1% | 18.3% | 13.6% | 20.4% | |

TABLE 11

Relative sensitivities of Pd and Ru promoted GDC sensors to 1% H$_2$ in simulated air with 0.5 vol % CH$_4$ vs temperature.

| Ex. | Formulation | Promoter | 250° C. | 275° C. | 300° C. | 350° C. | 400° C. | 450° C. |
|---|---|---|---|---|---|---|---|---|
| 8  | GDC (5.0 wt % SnO$_2$)  | none     | 10.6% |       | 4.60% | 22.0% | 7.93% |       |
| 15 | GDC (5.0 wt % SnO$_2$)  | 1 wt % Pd | 43.4% |       | 46.3% | 41.4% | 25.2% | 26.7% |
| 16 | GDC (5.0 wt % SnO$_2$)  | 1 wt % Ru | 15.7% |       | 11.3% | 12.9% | 20.5% |       |
| 10 | GDC (5.0 wt % In$_2$O$_3$) | none   | 11.2% |       | 12.7% | 23.2% | 8.70% | 8.70% |
| 17 | GDC (5.0 wt % In$_2$O$_3$) | 1 wt % Pd |     | 42.5% | 44.4% | 32.8% | 30.1% | 28.8% |
| 18 | GDC (5.0 wt % In$_2$O$_3$) | 1 wt % Ru |     | 21.2% | 17.8% | 12.8% | 22.0% |       |

Figure 6:
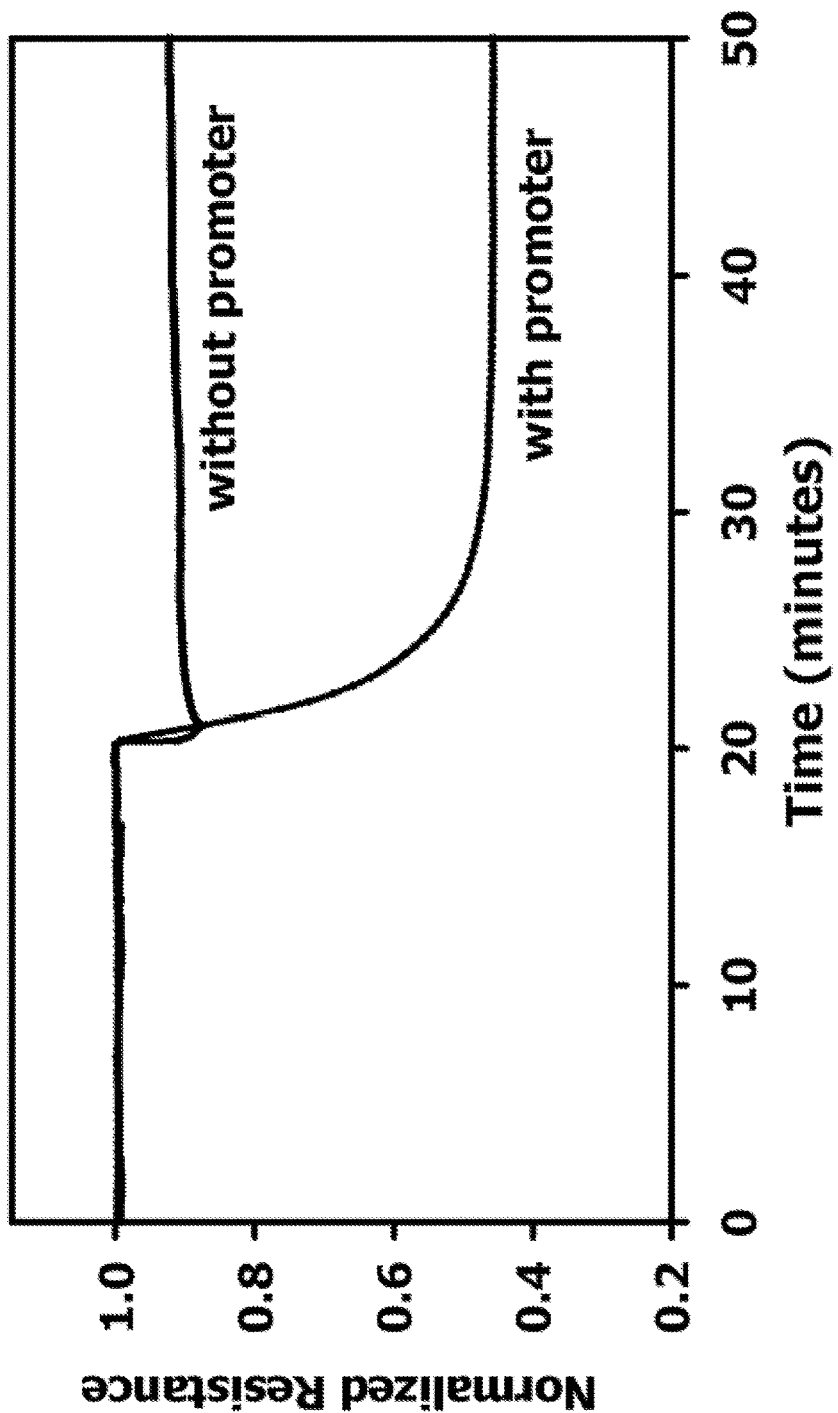
FIG. 6 is a graph of the effect of 1% Pd addition on $H_2$ sensitivity of the GDC (5% $SnO_2$) sensors of EXAMPLES 8 and 15 at 250° C.
Figure 7:
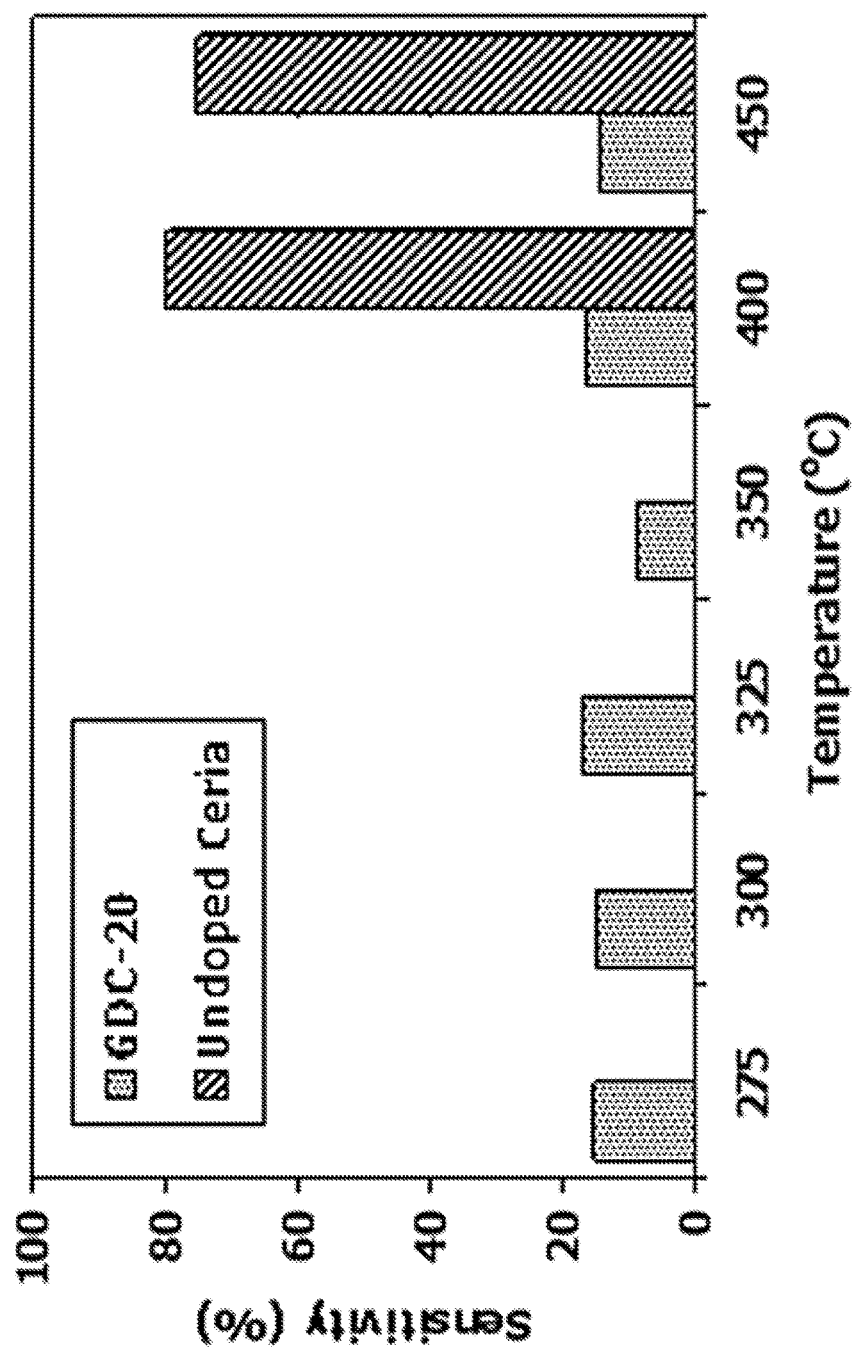
FIG. 7 is a graph of the effect of 1 wt % Pd on $H_2$ sensitivity of GDC (5% $SnO_2$) sensors of EXAMPLES 8 and 15 between 250 and 500° C.

For GDC based sensors, the presence of a palladium or ruthenium promoter increased hydrogen sensitivity. The largest improvement was observed for palladium addition, as shown in FIG. 6 for the Pd-doped GDC (5% SnO$_2$) sensor of EXAMPLE 15. The Pd addition to GDC (5% SnO$_2$) sensors enhanced sensitivity to 1% H$_2$ by about a factor of four; this enhancement was observed over a wide range of operating temperatures as shown in FIG. 7. The 94% GDC/5% SnO$_2$/1% Pd sensor formulation of EXAMPLE 15 was selected based on these results for further EXAMPLES to demonstrate prototype sensor elements.

Work to demonstrate prototype sensor elements focused on two types of sensor elements. The first type of sensor element used the described planar alumina substrate with the coating material deposited on the inter-digital electrodes and a resistive heater applied to the back side of the substrate. The second type of sensor element used a novel tubular substrate in which electrodes and the sensor coatings were applied to the outside surface of a ceramic micro-tube and a resistive wire heater was inserted into the inside of the tube.

As described in EXAMPLE 19, performance of the planar device was limited by the inefficiency of the internal heater. The internal heater effectively provided a controlled temperature for the planar device but also lost heat to its surroundings. The structural bonding of the heater to the planar element, which may be achieved in the "hot zone," also may lead to performance limitations related to long-term degradation of the bond. The planar device may also have a potential limitation related to differences in the thermal expansion coefficients of the aluminum oxide substrate, about 8 ppm/° C., and the ceria-based sensor coating, about 13 ppm/° C., that could result in failures during start-up and shut-down.

The tubular sensor device described in EXAMPLE 20 overcame these limitations, as noted below:

- The support component for the sensor was a porous ceramic tube with essentially the same composition (95% GDC/5% SnO$_2$) as the sensor coating material (94% GDC/5% SnO$_2$/1% Pd). Pd was omitted from the support material to minimize cost.
- The heat for the tubular sensor was provided by a wire heater located in the interior of the tube. Essentially all of the heat provided by the heater heated the element and very little heat is lost to the surrounding environment.
- The heater wire was bonded to the tube ends of the tubular sensor element, which are at a lower temperature compared to the sensor element during operation. The bonding was a non-structural bond and may be less prone to failures caused by thermal expansion mismatch.
- The micro-tubular element provides a high surface to volume ratio compared to planar devices, which may lead to improved sensitivity compared to planar devices. The improved sensitivity resulted in lower operating temperatures, and better long-term stability of baseline resistance and H$_2$ sensitivity.
- The resistance of the heater in the micro-tubular element may be selected to minimize the sensitivity of the sensor device to variation in relative humidity.
- Although thermal expansion match may be higher, other support tubes materials such as aluminum oxide and YSZ may be used, offering advantages such as cost, strength, and insulating properties.

The following examples illustrate the advantages of the tubular sensor structure.

Example 19: Planar Hydrogen Sensor Element

Figure 8:
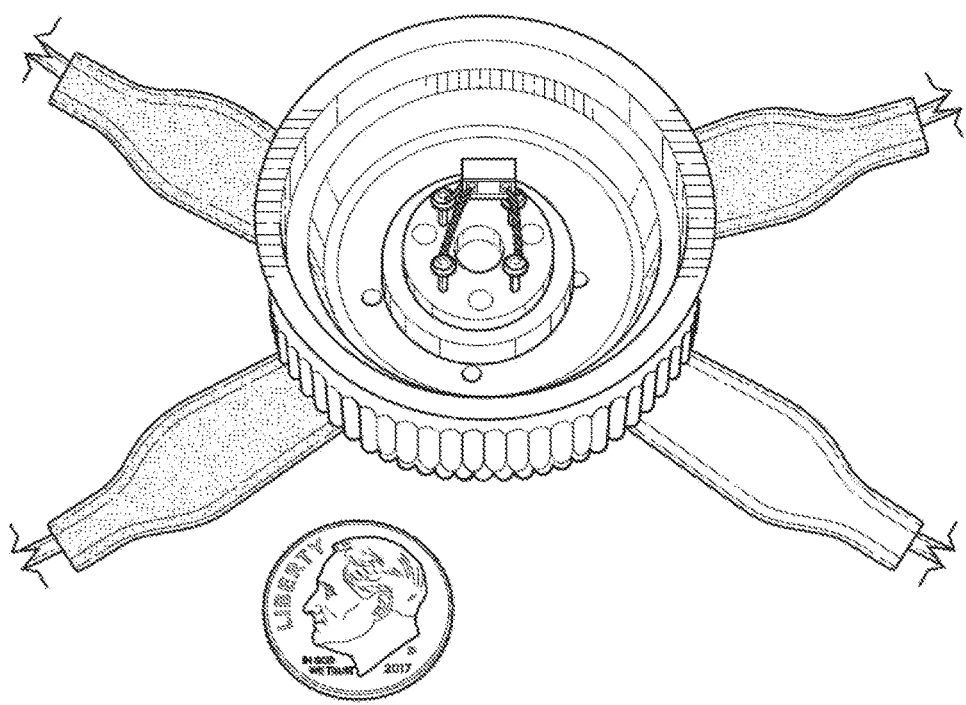
FIG. 8 is an image of an exemplary $H_2$ sensor of EXAMPLE 19.
Figure 9:
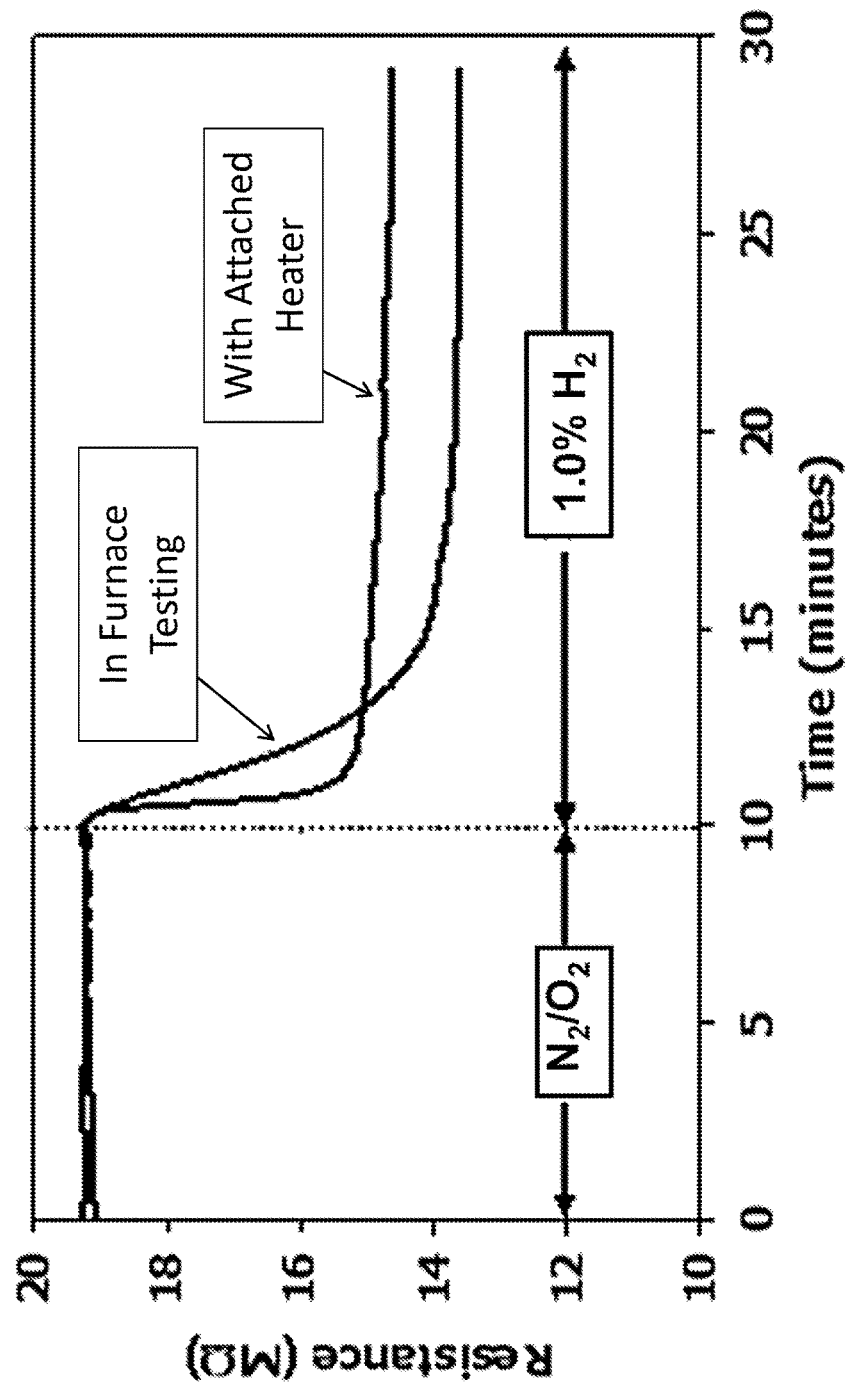
FIG. 9 is a graph of $H_2$ sensing by the $H_2$ sensor of EXAMPLE 19.

A coating of the selected sensor material (94% GDC/5% SnO$_2$/1% Pd) was deposited onto an IDE substrate (5-mm square) and annealed at 800° C. for one hour. An 8.1Ω resistive heater was fabricated from a 34 AWG nickel-chromium 60 resistive heating wire. The 8.1Ω resistive heater was bonded to the back side of the IDE substrate using ceramic cement (CERAMABOND™ 552-VFG high temperature ceramic adhesive, Aremco, Valley Cottage, N.Y.). The planar sensor element is shown in FIG. 8. The performance of the sensor element (baseline resistance and H$_2$ sensitivity) was first tested in a tube furnace at 300° C. (the desired operating temperature based on previously described results) with externally supplied heat (with the attached heater not energized). The sample was then removed from the tube furnace and mounted on a TO8 header to provide the electrical connections to the heater and sensor electrode leads. This stand-alone prototype was tested in another enclosure with feedthroughs for both the sensor leads and the heater contacts. Power was applied to the resistive heater on the backside of the IDE substrate and increased until the baseline resistance of the sensor was the same as when measured with heat being externally supplied by the tube furnace. Approximately 2.8 watts of power was used to heat the sensor element to target baseline resistance (19 MΩ). The performance of the sensor operating with an internal heater then was compared to that obtained with external heating. These data are presented in FIG. 9.

The performance of the sensor with internal heating was similar to the performance with external heating, although the response to 1% hydrogen was slightly greater and response was slightly slower when the sensor was tested with external heating. The slower response observed when testing with external heating was due to a much larger dead space in the quartz tube compared to the test fixture used once the sensor was mounted on the header and tested with the onboard heater. The loss in sensitivity may be explained by the kinetic difference of sensing heated gas versus sensing an ambient temperature gas. The tube furnace provided heat to both the sensor and the gases surrounding the sensor, while the resistive heater supplied heat directly to the sensor and not to the surrounding gas.

Figure 10:
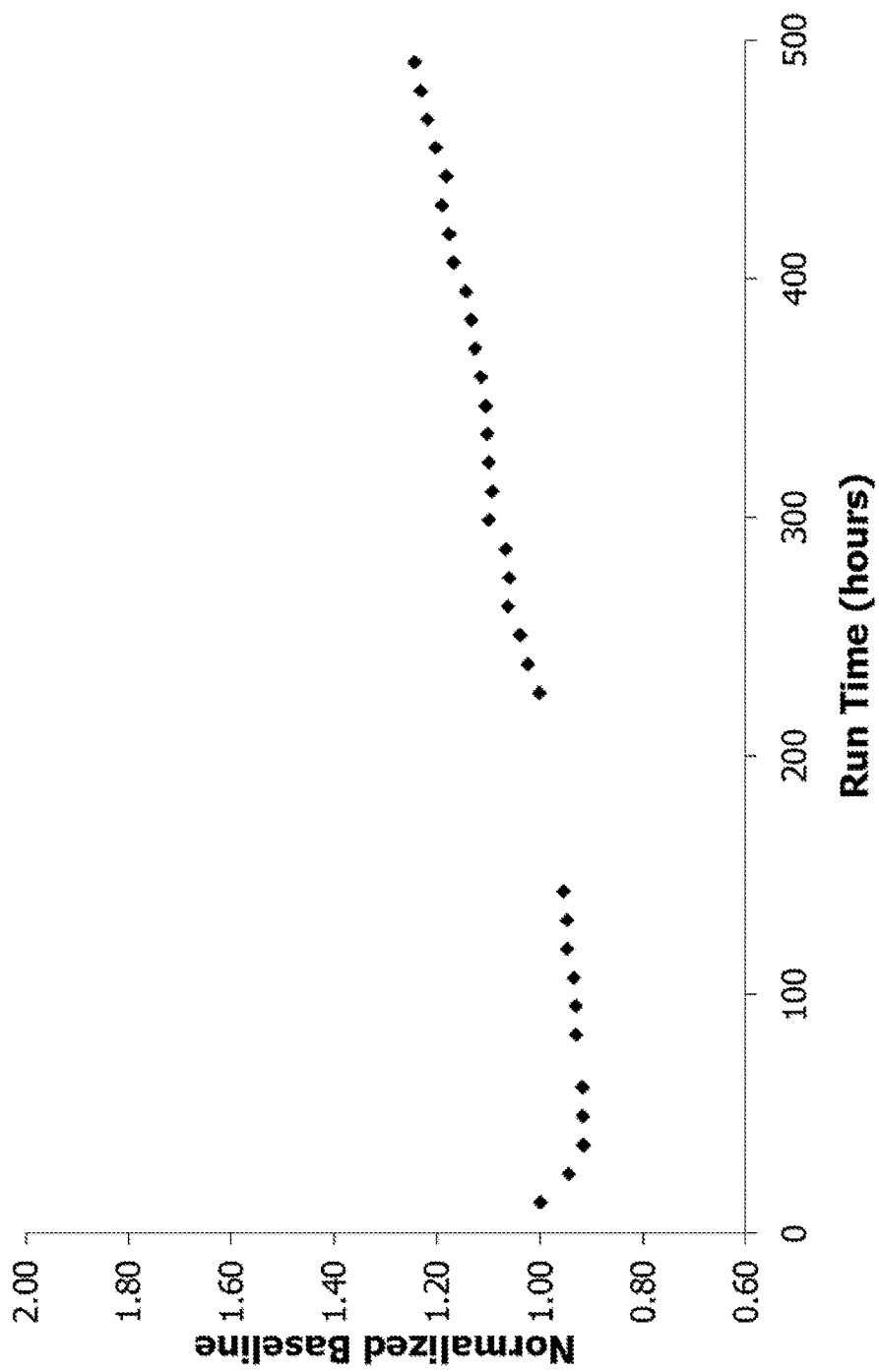
FIG. 10 is a graph of long-term baseline resistance drift of the sensor of EXAMPLE 19.
Figure 11:
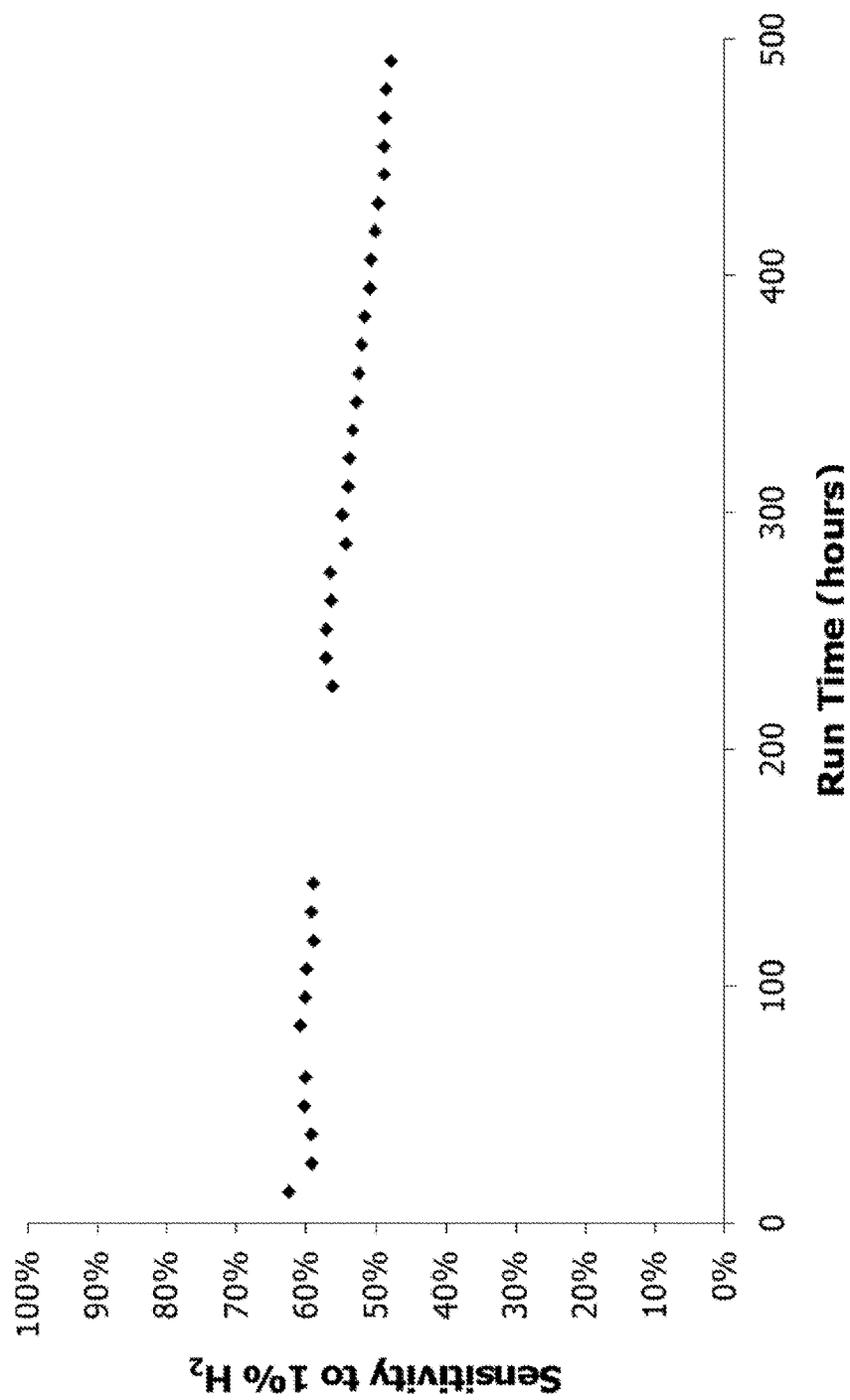
FIG. 11 is a graph of long-term drift of $H_2$ sensitivity of the sensor of EXAMPLE 19.

Long-term tests were conducted on planar sensors to evaluate the stability of the baseline resistance and sensitivity during cycling in air between 0 and 1% $H_2$ (12-hour cycle times). These tests were conducted on a planar element, made through previously described methods, with external heat supplied by a tube furnace. Long-term stability data are presented in FIGS. 10 and 11. Over the course of this 500 hour test, the baseline resistance had increased by approximately 25 percent and the sensitivity had decreased from 60 to 48 percent for this planar sensor.

Example 20: Tubular Hydrogen Sensor Element

Figure 13:
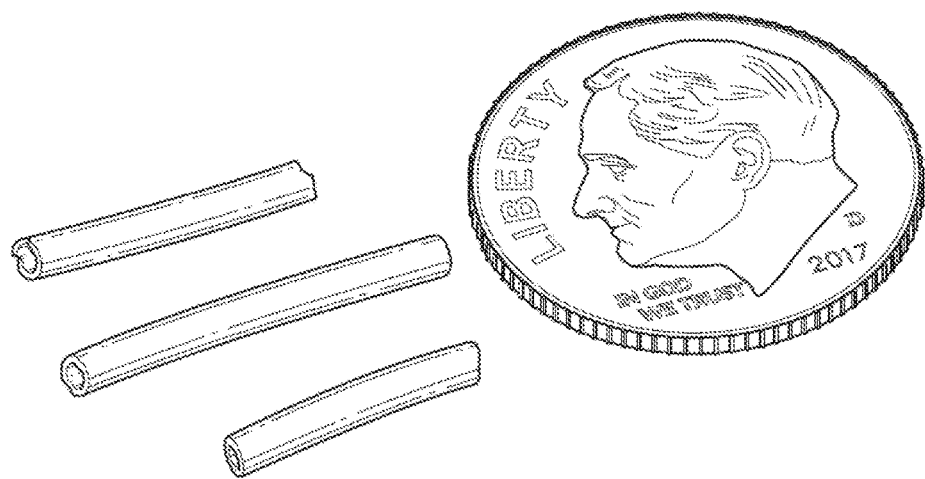
FIG. 13 is an image of exemplary sintered porous ceramic micro-tubes of the GDC (5% $SnO_2$) composition of EXAMPLE 20.

Prototype micro-tubular sensors were fabricated, integrated with NiCr heaters, and tested for hydrogen sensitivity. A general schematic showing the manufacturing steps for the micro-tubular sensor elements is shown in FIG. 12. A 50-gram batch of the GDC (5% $SnO_2$) powder with a surface area of 14 $m^2$/gram was prepared for extrusion of support tubes. A thermal plastic dough was mixed using this composite material through the addition of conventional binders and plasticizers, and extruded using a capillary rheometer (Bohlin Instruments RH2000, Malvern, United Kingdom). The tubes were dried and then sintered at 1100° C. The sintered micro-tubes were about 65% theoretical maximum density. The 65% density was considered to be in the ideal range for the sensor—sufficiently dense to provide mechanical ruggedness, yet sufficiently porous to provide a rough surface for optimum adhesion of subsequently deposited coatings. After sintering, the micro-tubes had an outside diameter of 1.5 mm and a wall thickness of 0.5 mm. The sintered tubes are shown in FIG. 13.

Figure 14:
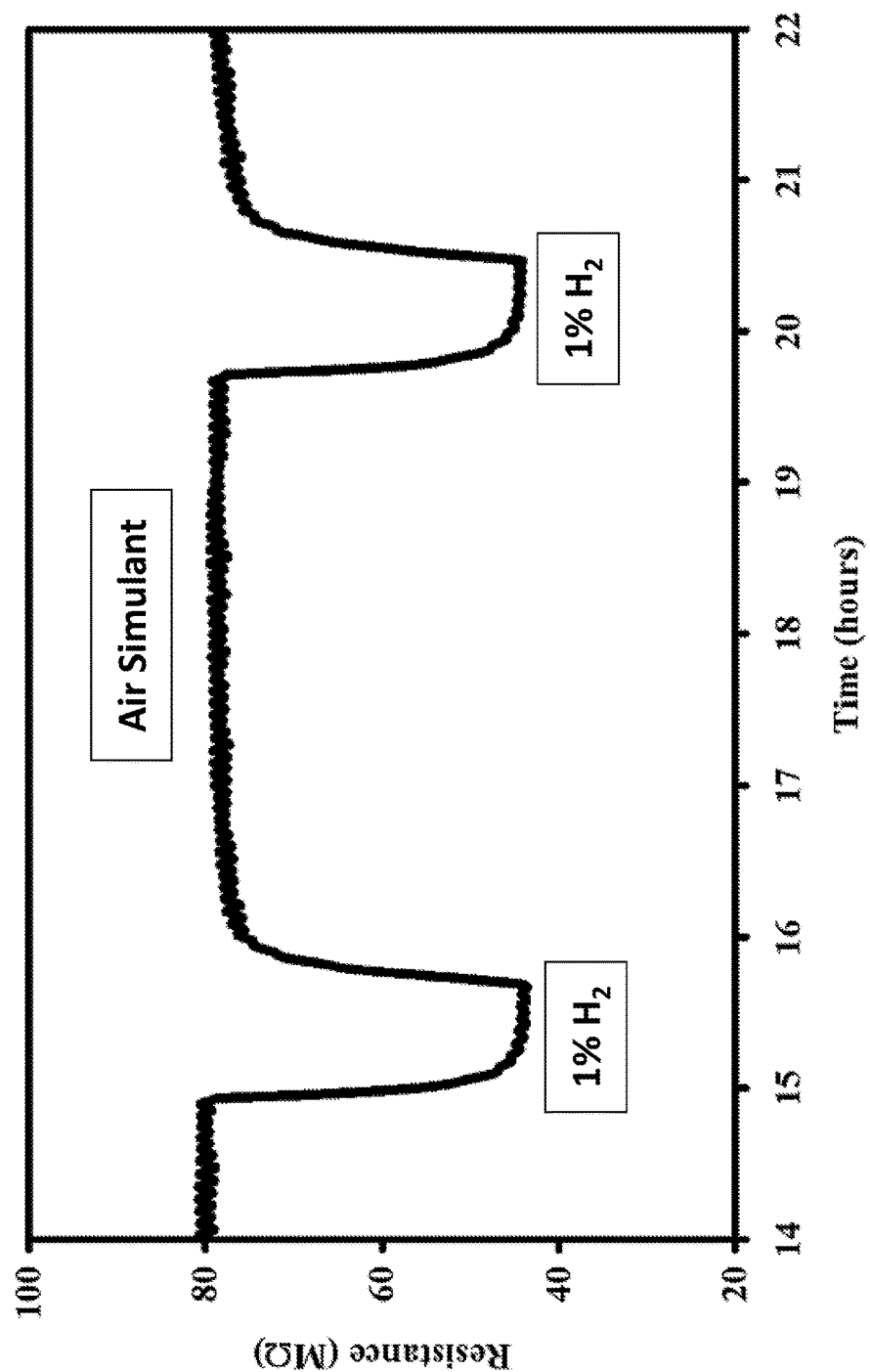
FIG. 14 is a graph of $H_2$ sensitivity of the tubular sensor of EXAMPLE 20 at 175° C.

Tubular sensors were fabricated from sintered 5% $SnO_2$-GDC tubes in the following manner: (1) silver lead wires were attached to the exterior of the tube using silver ink; (2) gold electrodes were painted on the tube, connected to the silver leads, and cured at 450° C. for 30 minutes; and (3) the sensor material was painted on the exterior of the tube and annealed at 800° C. for one hour. Performance of the tubular sensor elements without internal heaters was evaluated in a tube furnace using the same testing conditions described herein. The optimum operating temperature for the sensor was lowered from 300 to 200° C. based on maximum sensitivity to 1% $H_2$. Testing of the sensor at temperatures as low as 175° C. still showed strong responses to 1% hydrogen, as shown in FIG. 14.

Figure 15:
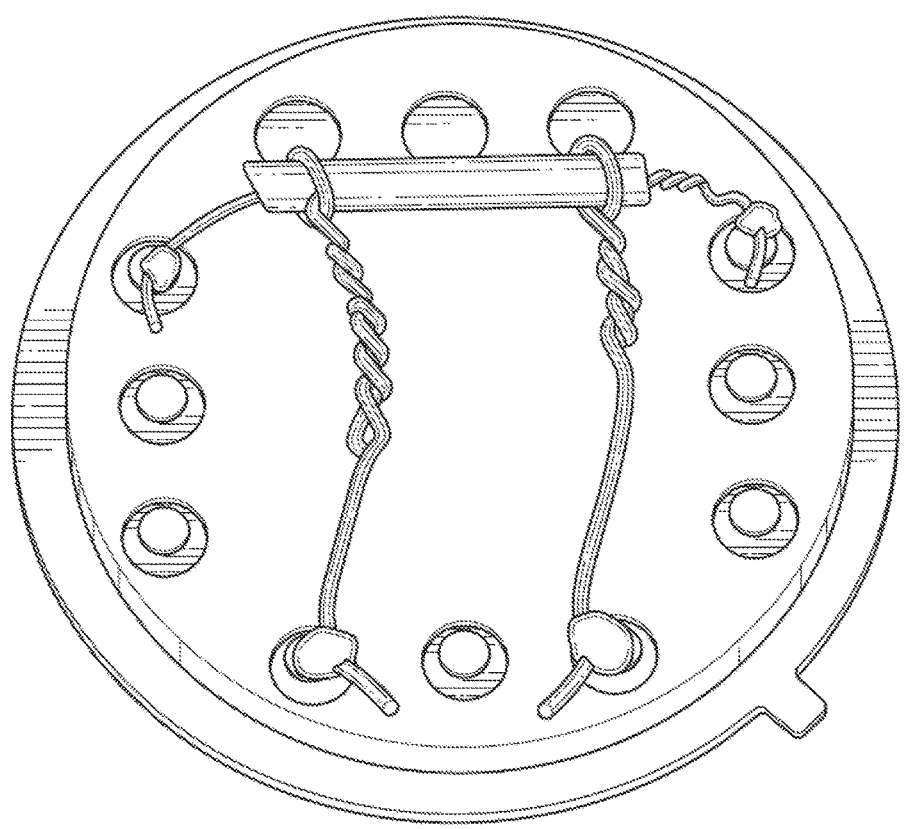
FIG. 15 is an image of an exemplary micro-tubular $H_2$ sensor with internal heater as described in EXAMPLE 20.

Multiple prototype tubular sensors were fabricated and tested. The internal heaters were made from 51 lengths of 34 AWG nichrome-60 heater wire by tightly coiling the wires. The coil heaters were designed so that the outside diameter of the coil would allow the heater to fit inside of the extruded micro-tube. A tubular sensor element is shown in FIG. 15. The performance of tubular prototype sensors was evaluated by applying various amounts of power to the internal heater and evaluating baseline resistance, $H_2$ sensitivity and cross-sensitivity using methods described herein. A heater power of only 750 mW was used to achieve a baseline resistance of 20 MΩ, corresponding to an estimated operating temperature of 200° C. Also, 615 mW of heater power was used to achieve a baseline resistance of 80 MΩ, corresponding to an estimated operating temperature of 175° C. Sensor performance within this range of heater power exceeded that of the planar sensor of EXAMPLE 19. The tubular structure reduced power consumption compared to the planar sensor of EXAMPLE 19 by more than 70 percent.

Example 21: Tubular Hydrogen Sensor Elements with Alumina and YSZ Substrates

Figure 16:
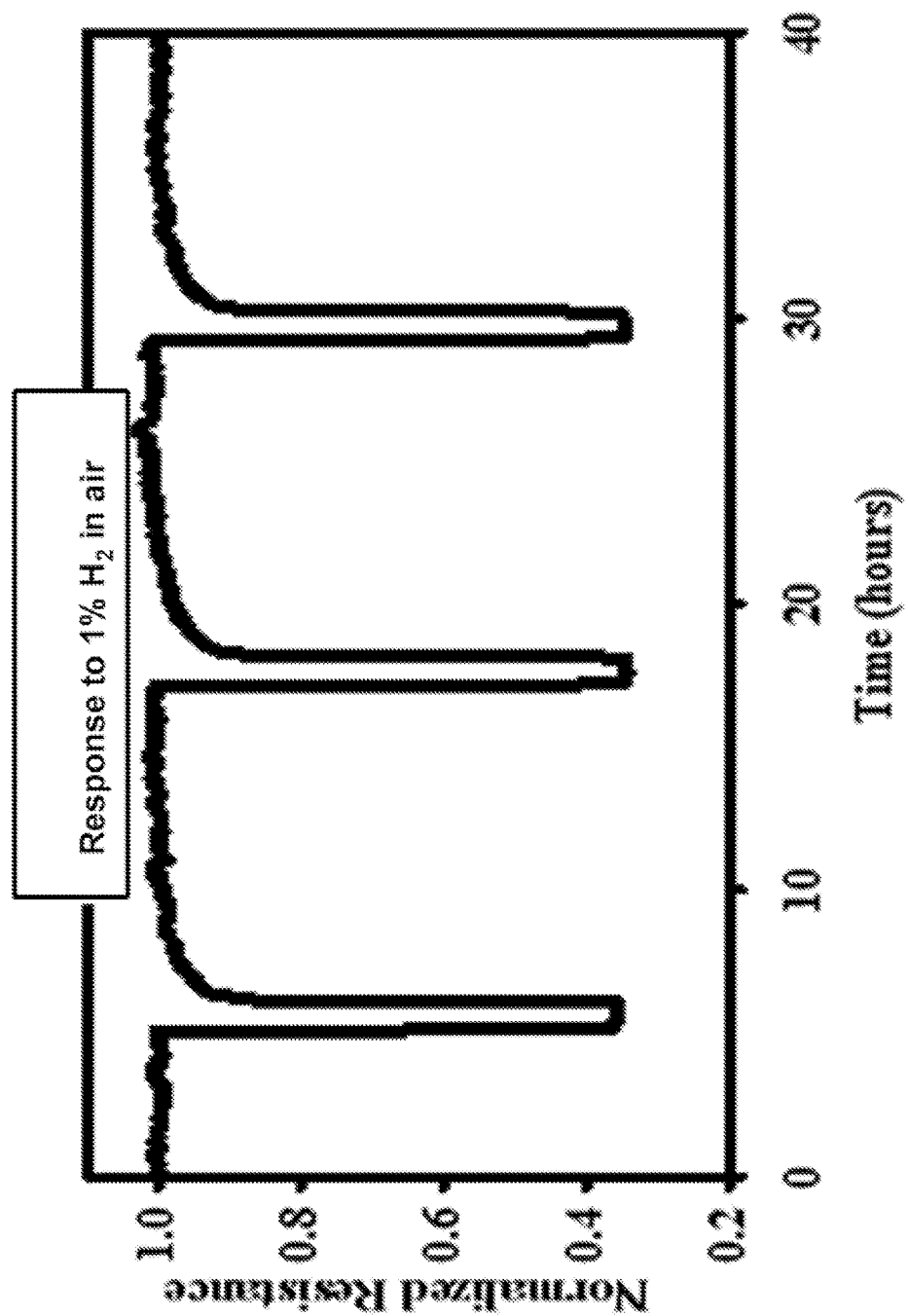
FIG. 16 is a graph of $H_2$ sensing by the micro-tubular $H_2$ sensor of EXAMPLE 21.
Figure 17:
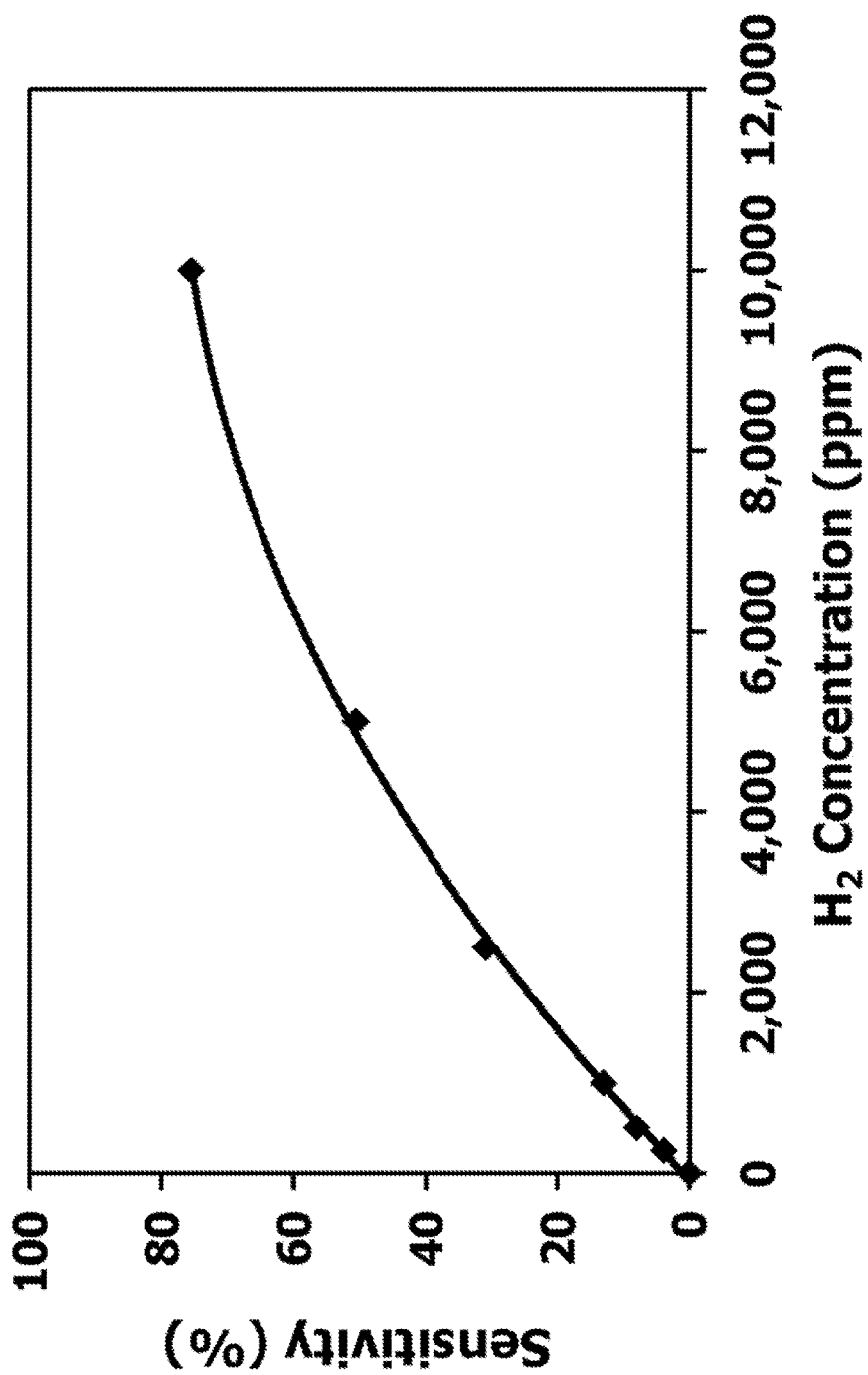
FIG. 17 is a graph of the quantitative response of the tubular sensor of EXAMPLE 21.

Purchased aluminum oxide and 8 mol % yttria-stabilized zirconia tubes were cut to 8 mm lengths. The alumina tubes had an outside diameter of 1 mm and wall thickness of 0.5 mm. The YSZ tubes had an outside diameter of 4.4 mm and wall thickness of 0.4 mm. Sensors were fabricated from these substrates using methods described in EXAMPLE 20. Approximately 40Ω heater wire lengths were used for the alumina substrate sensors and approximately 10Ω wire lengths were used for the YSZ substrate sensors. The performance of the tubular sensor showed significant improvements over the planar sensor of EXAMPLE 19. An average response of greater than 60% was demonstrated when the sensor was exposed to one percent hydrogen in a dry simulated air background, a 50% improvement over the planar sensor of EXAMPLE 19. Data collected from three hydrogen cycles is shown in FIG. 16. The sensor exhibited quantitative responses over a range of hydrogen concentrations from 250 to 10,000 ppm as shown in FIG. 17.

The apparent response time of the tubular sensor also was improved over that of the planar sensor of EXAMPLE 19. The response time $t_{90}$ is defined as the time it takes for the signal of the sensor to reach 90% of the full response. The $t_{90}$ for 1% hydrogen of the planar prototype sensor of EXAMPLE 19 was 2.3 minutes, whereas the $t_{90}$ for the tubular prototype sensor was only 20-30 seconds. Another key feature of the tubular sensor was a fast recovery time. The $t_{90}$ for the recovery of the sensor was less than 50 seconds.

Figure 18:
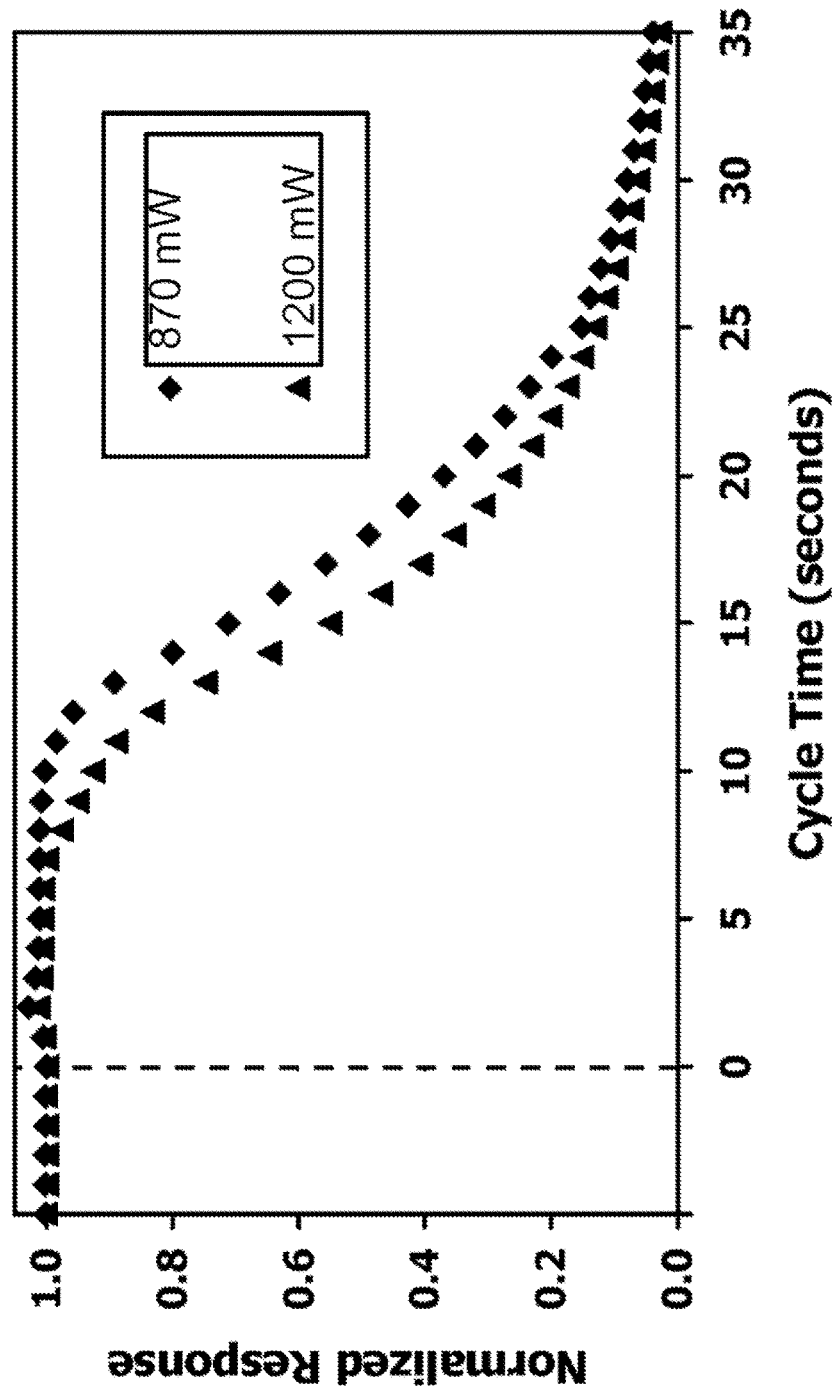
FIG. 18 is a graph of the effect of heater power (operating temperature) on response time of the micro-tubular sensor of EXAMPLE 21.

FIG. 18 shows response times of the tubular sensor operating at different heater powers. Kinetics of the surface reactions increased as more power, or heat, was applied to the sensor, which was anticipated to decrease the response time of the sensor. There was a measurable decrease in sensor response time when operating the sensor at higher heater powers. After subtracting the seven-second dead time, the $t_{90}$ for the sensor operated at 1200 mW was 20 seconds, compared to 23 seconds at 870 mW.

Figure 19:
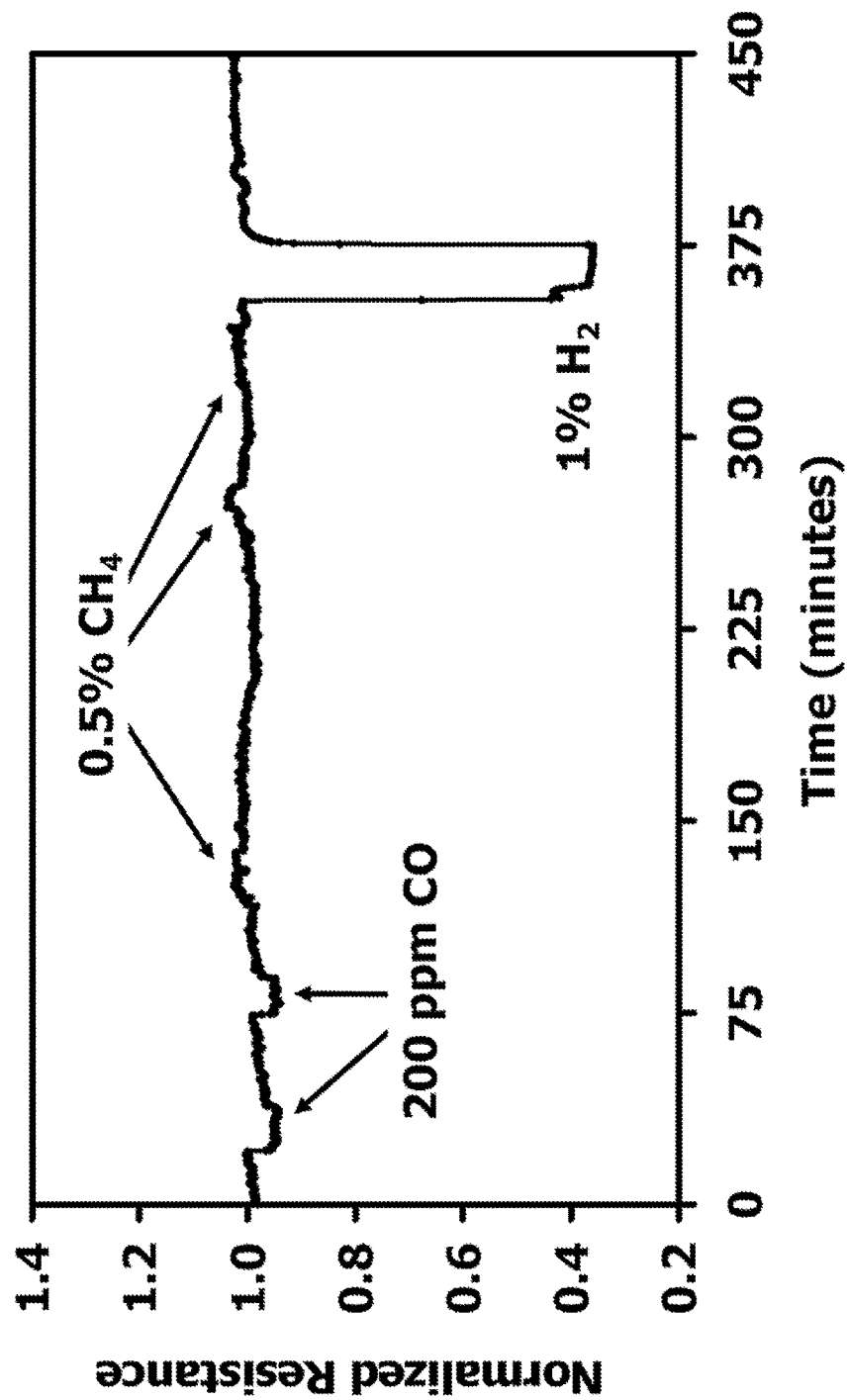
FIG. 19 is a graph of the interference resistance of the micro-tubular $H_2$ sensor of EXAMPLE 21.

The tubular prototype sensor also exhibited the same interference resistance to both CO and $CH_4$ as described herein. The sensor showed no response to $CH_4$ and only minimal movements in the baseline when exposed to 200 ppm CO. A plot of the raw data of the sensor signal is shown in FIG. 19. The interference caused by the cross sensitivity to CO was not much greater than baseline noise and could easily be tuned out by the sensor circuit design.

Figure 20:
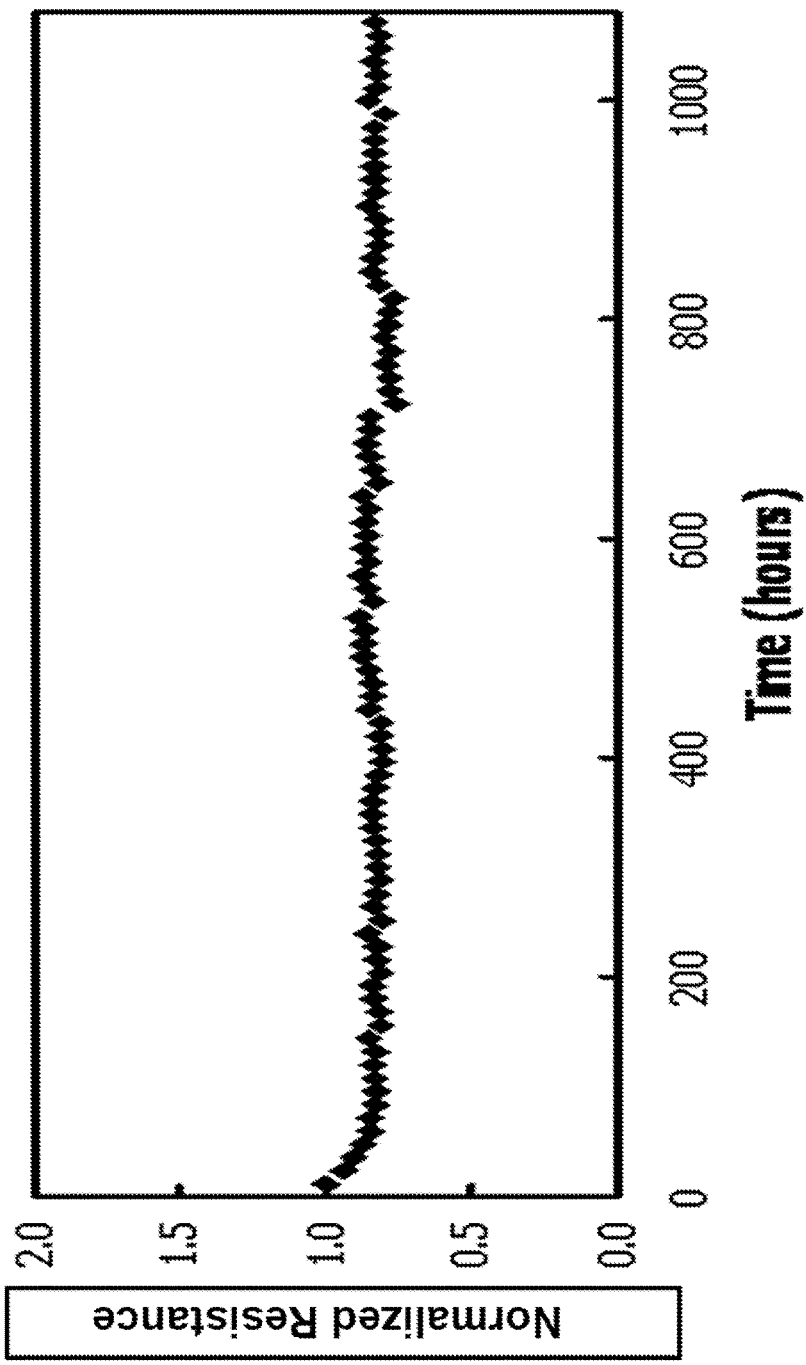
FIG. 20 is a graph of baseline resistance versus time for the micro-tubular $H_2$ sensor of EXAMPLE 21.
Figure 21:
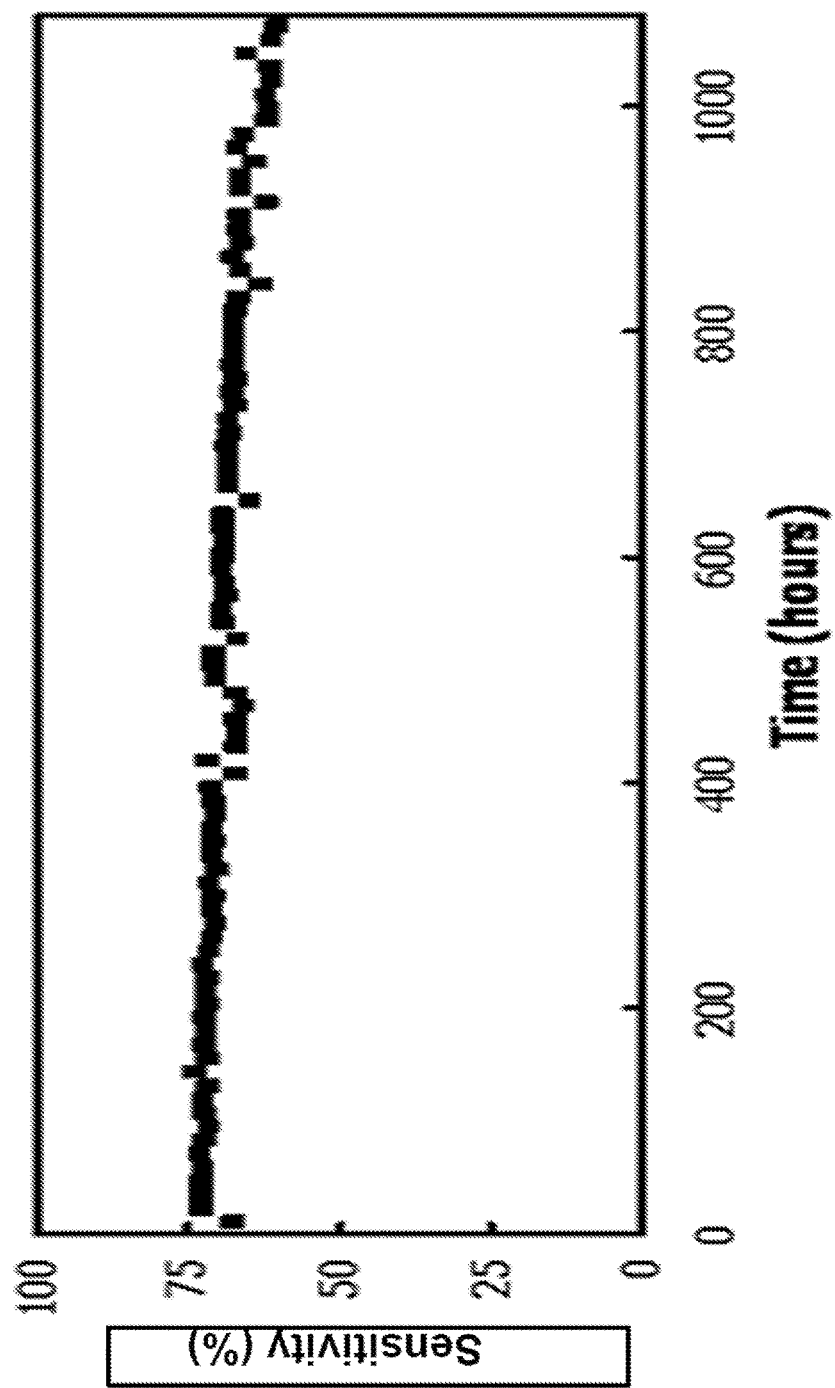
FIG. 21 is a graph of sensitivity to 1% $H_2$ versus time for the micro-tubular $H_2$ sensor of EXAMPLE 21.

A long-term test was completed for a tubular sensor, with results presented in FIGS. 20 and 21. The long-term testing was conducted in a tube furnace at a controlled temperature of 200° C. The baseline resistance and sensitivity of the tubular sensor were remarkably stable over 600 hours of testing, with essentially no increase of baseline resistance or loss of sensitivity. The increased stability compared to the planar sensors was due to the lower operating temperature of the tubular sensor, about 200° C. compared to about 300° C. for the planar sensors. Such lower temperatures may reduce aging effects, which may occur via a thermally activated sintering mechanism. Sintering may result in reduced gas accessibility to grain boundaries, which may be the primary active sites for the sensor.

Figure 22:
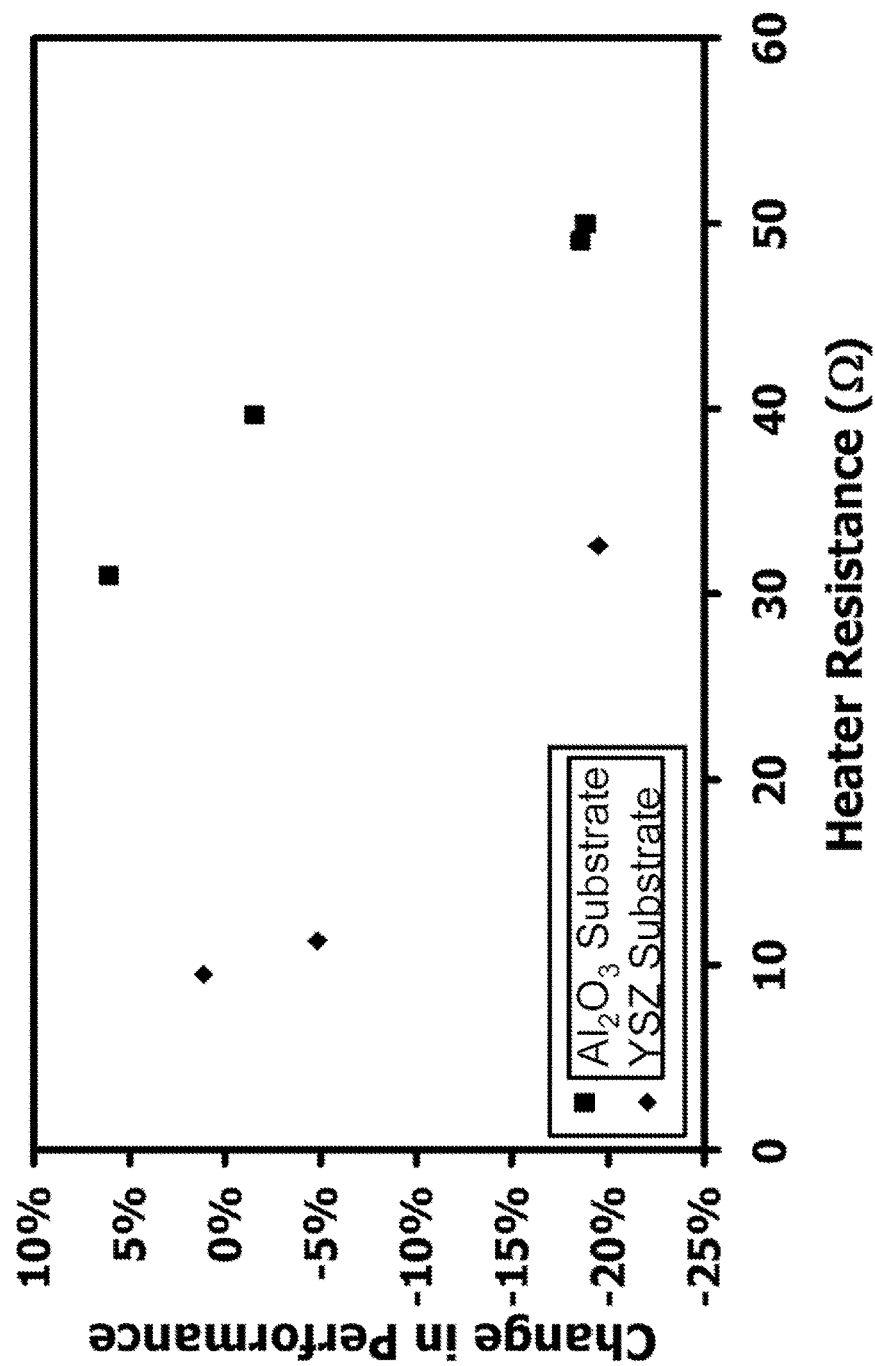
FIG. 22 is a graph of the change in sensor performance upon a change in relative humidity from 0% to 100% as a function of heater resistance for both aluminum oxide and yttria stabilized zirconia micro-tubular substrate sensors.
Figure 23:
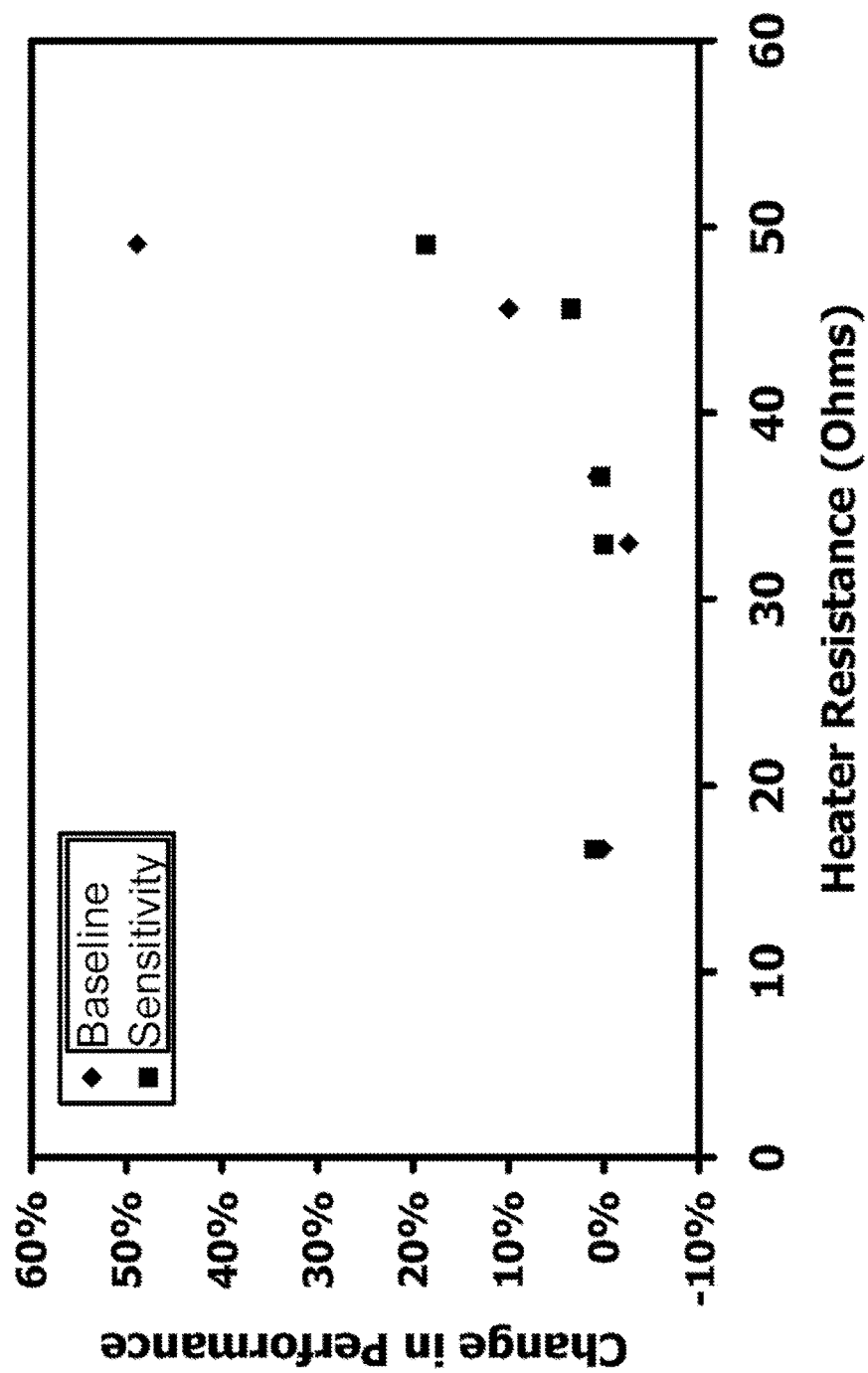
FIG. 23 is a graph of the change in sensor baseline resistance and sensitivity to 1% $H_2$ upon a change in relative humidity from 0% to 100% for aluminum oxide micro-tubular substrate sensors.
Figure 24A:
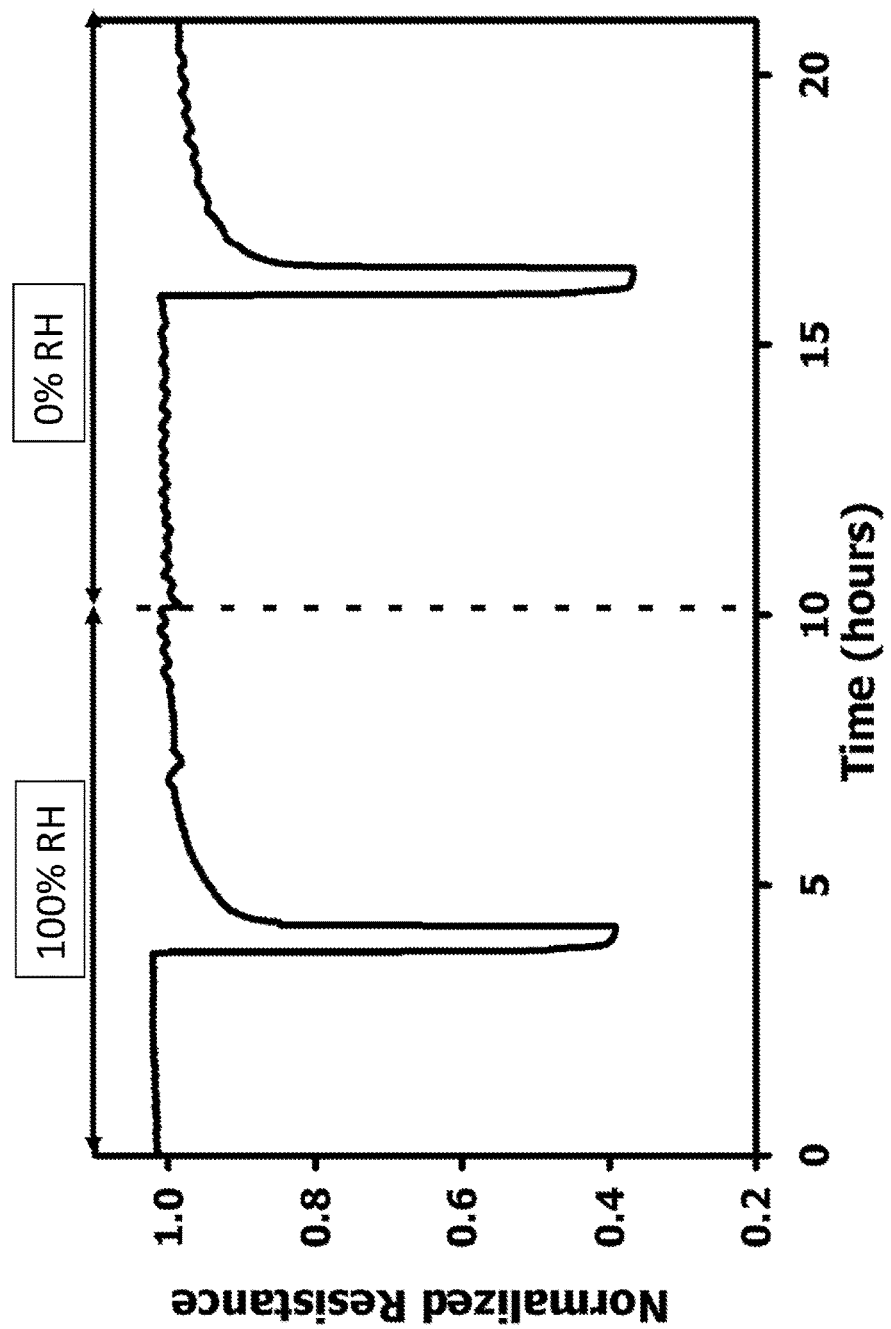
FIG. 24A is a graph of the response characteristics of an aluminum oxide micro-tubular substrate sensor with a 39.7Ω heater upon a change in relative humidity from 0% to 100%.
Figure 24B:
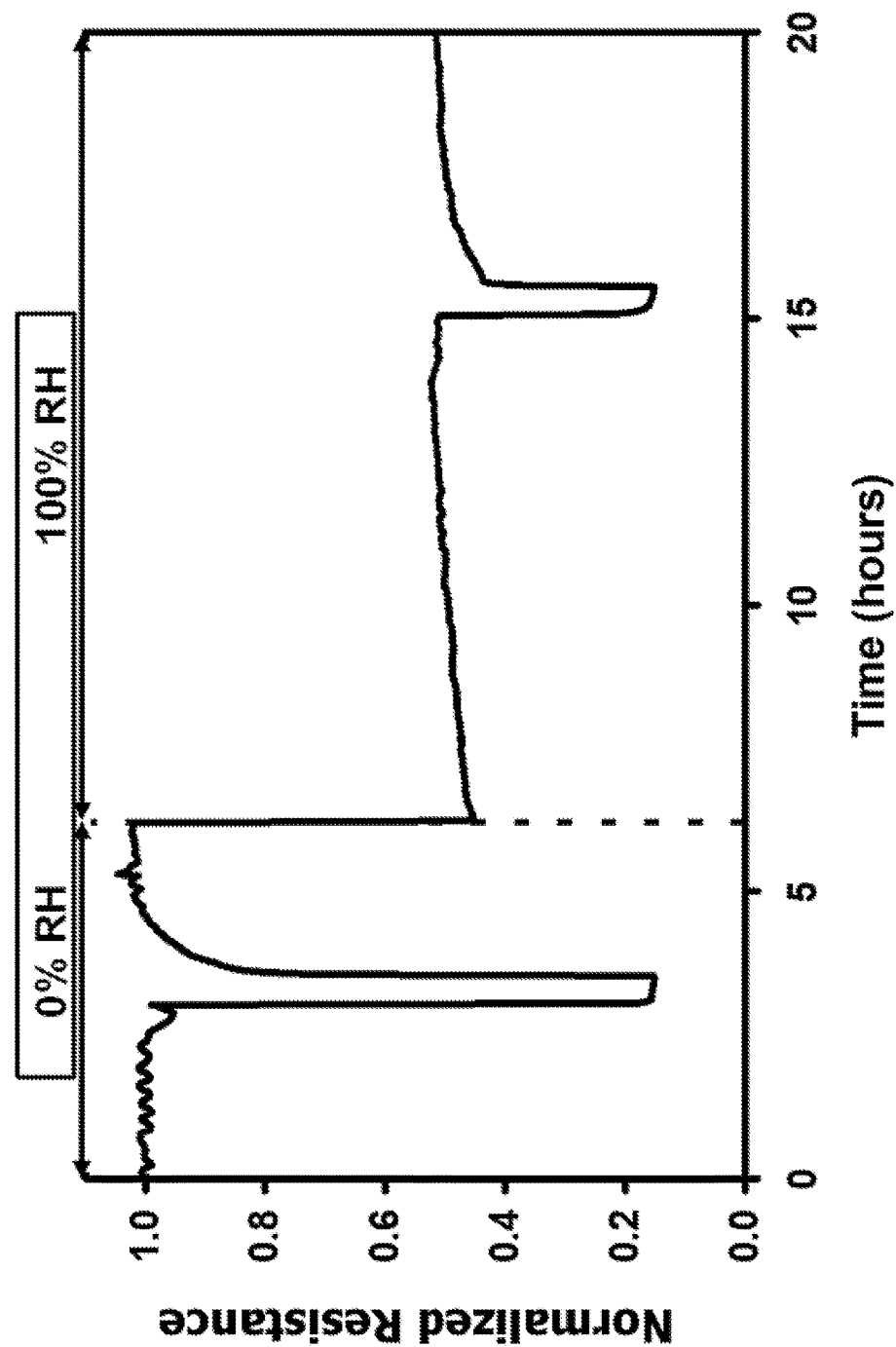
FIG. 24B is a graph of the response characteristics of an aluminum oxide micro-tubular substrate sensor with a 49.1Ω heater upon a change in relative humidity from 0% to 100%.

Prototype tubular sensors were fabricated with varying heater resistance and tested for effects of relative humidity variation on sensor baseline resistance and sensitivity to hydrogen. Sensors were tested for sensitivity to 1% hydrogen in both dry, 0% relative humidity, and wet, 100% relative humidity environments. The internal heaters were made from lengths of 40 AWG nichrome-60 heater wire by tightly coiling the wires. Heaters ranging from 30 to 50Ω were inserted into sensors with aluminum oxide tubular substrates. Heaters ranging from 9 to 35Ω were inserted into sensors with yttria stabilized zirconia (YSZ) tubular substrates. The coil heaters were designed so that the outside diameter of the coil would allow the heater to fit inside of the extruded micro-tube. FIG. 22 shows the effects of heater resistance on both baseline resistance and sensitivity to 1% hydrogen for both aluminum oxide and YSZ substrates. In the alumina oxide substrate sensors, heater resistance near 30Ω minimized the effects of humidity variation, while in the YSZ substrate sensors, much lower resistance heaters were used for the same humidity insensitivity. This relationship between heater resistance and humidity sensitivity was further explored by testing alumina substrate sensors with heaters as low as 15Ω (FIG. 23). A non-linear relationship was observed, with sensors having negligible sensitivity to humidity variation with heater resistance approximately less than 40Ω. With higher resistance heaters, humidity greatly impacted sensor performance. FIG. 24A shows the negligible effects of humidity on a 39.7Ω resistance heater sensor compared to the large humidity sensitivity of a 49.1Ω heater sensor shown in FIG. 24B.

Figure 25:
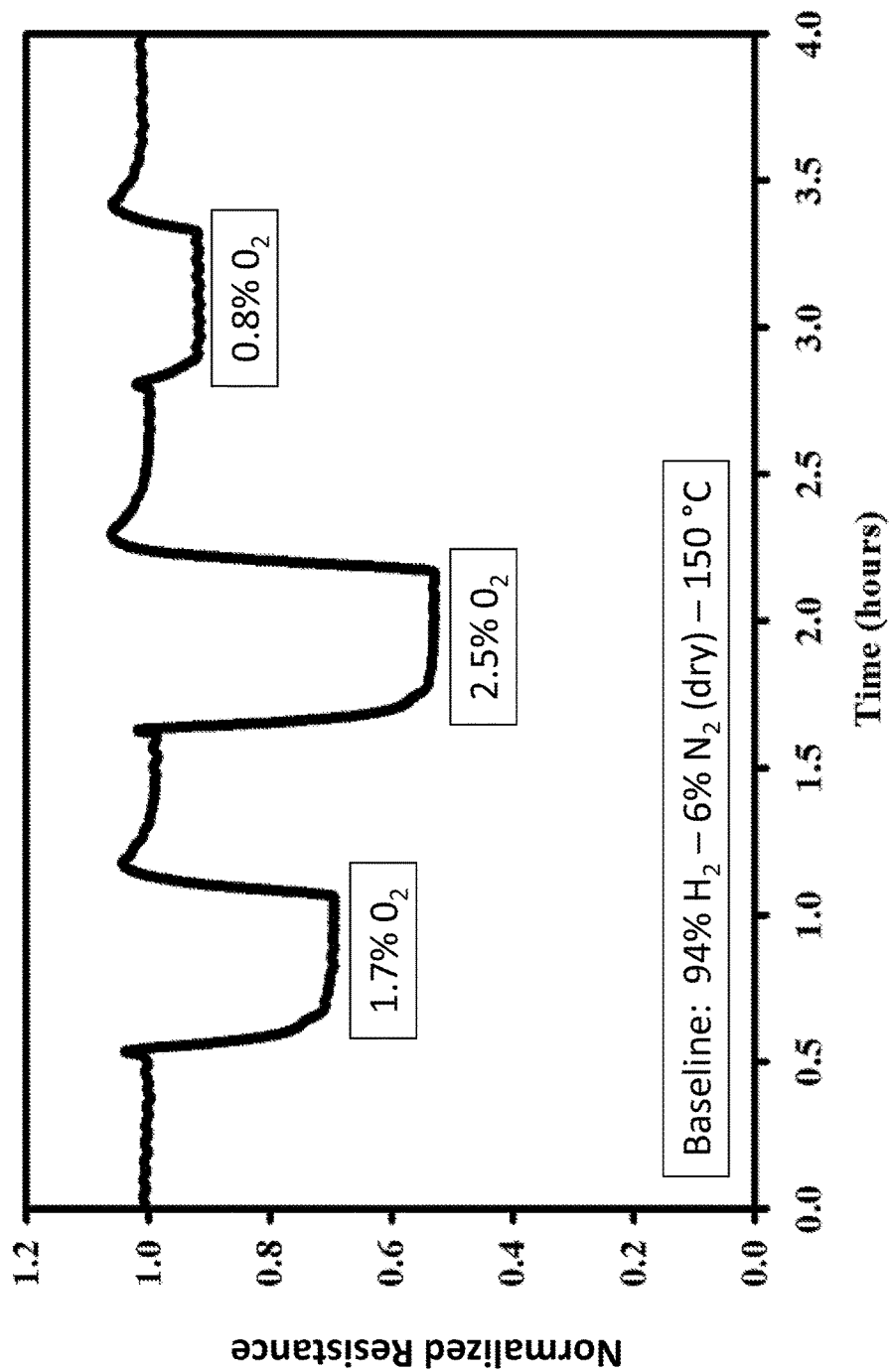
FIG. 25 is a graph of the quantitative detection of $O_2$ in $H_2$ using the micro-tubular $H_2$ sensor of EXAMPLE 21.

The micro-tubular sensor of this EXAMPLE was also found to be useful in quantitatively detecting the presence of small amounts of oxygen in ambient hydrogen. Data in FIG. 25 shows the sensor response with a high degree of sensitivity to varying oxygen concentrations in a hydrogen-rich background gas environment.

Example 22: Comparative Commercial Chemical Resistor Type Hydrogen Sensor

The performance of the micro-tubular hydrogen sensor was compared to that of a commercially available chemical resistor type hydrogen sensor. A TGS 821 sensor (Figaro USA, Inc., Arlington Heights, Ill.) was selected for the comparison. The TGS 821 has a tin oxide ($SnO_2$) based ceramic sensing element and is heated by a small resistive heater. The tin oxide based sensor has a relatively high resistance in clean air, but its resistance decreases in the presence of a detectable gas. The TGS 821 was obtained and tested in accordance with documentation received with the sensor. The heater on the sensor operates at approximately 650 mW, which is similar to the micro-tubular sensor of EXAMPLE 21.

Figure 26:
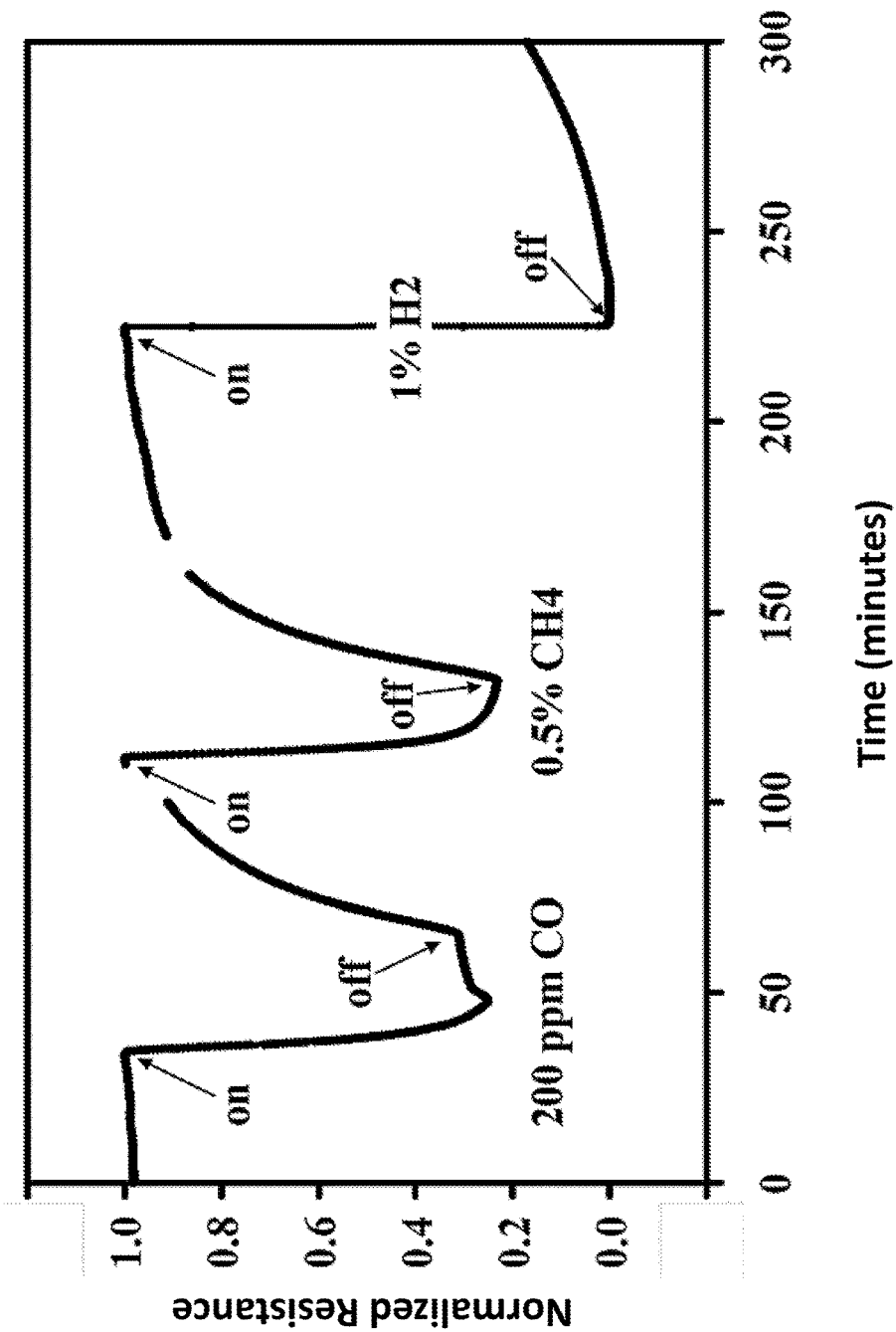
FIG. 26 is a graph of normalized responses of the sensor of comparative EXAMPLE 22 to 1% $H_2$, 200 ppm CO, and 0.5% $CH_4$.

The sensitivity of the TGS 821 sensor to 1% hydrogen matched the value reported in the product documentation. While the sensor was very sensitive to 1% hydrogen (greater than 99% response), it also showed very large responses to CO and $CH_4$ (see FIG. 26). The responses of 69% and 76% to 200 ppm CO and 0.5% $CH_4$, respectively, were consistent with values reported in the product documentation. By contrast, FIG. 19 shows that the sensor of EXAMPLE 21 displayed negligible cross sensitivity to these concentrations of CO and $CH_4$.

Figure 27:
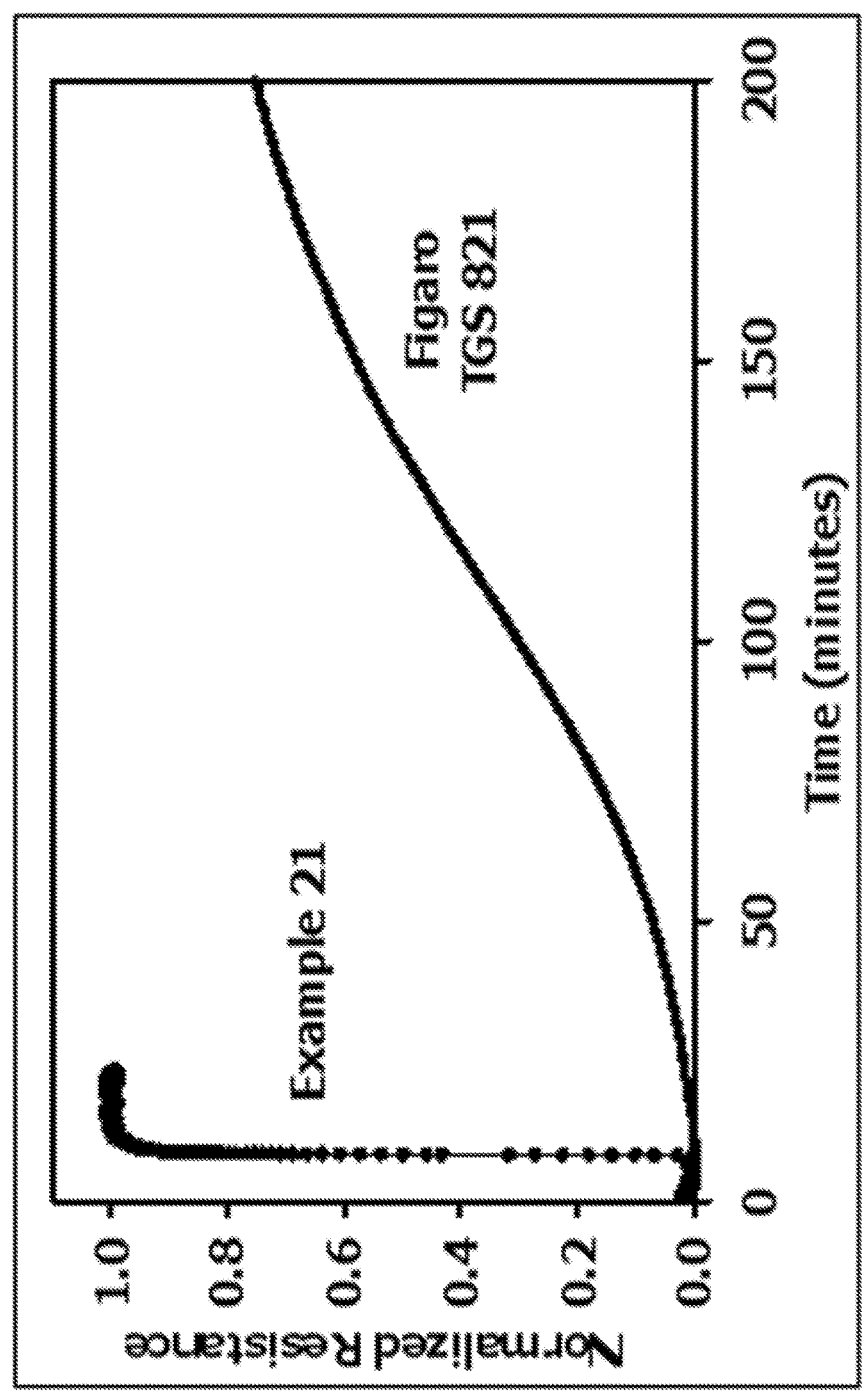
FIG. 27 is a graph of recovery times for the micro-tubular $H_2$ sensor of EXAMPLE 21 and the commercially available sensor of comparative EXAMPLE 22.

Response times for both the TGS 821 sensor and the micro-tubular sensor of EXAMPLE 21 were less than the application-specific target of thirty seconds (10 seconds for the TGS 821 sensor and 20 seconds for the micro-tubular sensor). Surprisingly, the recovery time of the micro-tubular sensor was much faster, as shown in FIG. 27. The micro-tubular sensor recovered to its original baseline within 48 seconds after hydrogen was removed, while the TGS 821 sensor had not recovered to 70 percent of its original baseline resistance after three hours. Another advantage of the micro-tubular sensor was rapid start-up time (less than 5 minutes). Start-up of the TGS 821 sensor was slow. The product documentation states that the standard test conditions include a seven day pre-heating period before testing the sensor.

The use of the disclosed micro-tubular sensor design for hydrogen sensing is not limited by the use of the disclosed ceria-based sensor coating materials. The disclosed micro-tubular sensor element design may be used for a chemical resistor type hydrogen sensor using any known hydrogen sensitive oxide (such as tin oxide), hydrogen sensitive metal (such as palladium), hydrogen sensitive combination of oxide and metal, or any material that exhibits a measurable response, e.g., resistive and/or capacitive, to hydrogen. The geometry of the tubular support for the sensor may be varied over a wide range according to manufacturability of the tubular component.

Figure 28:
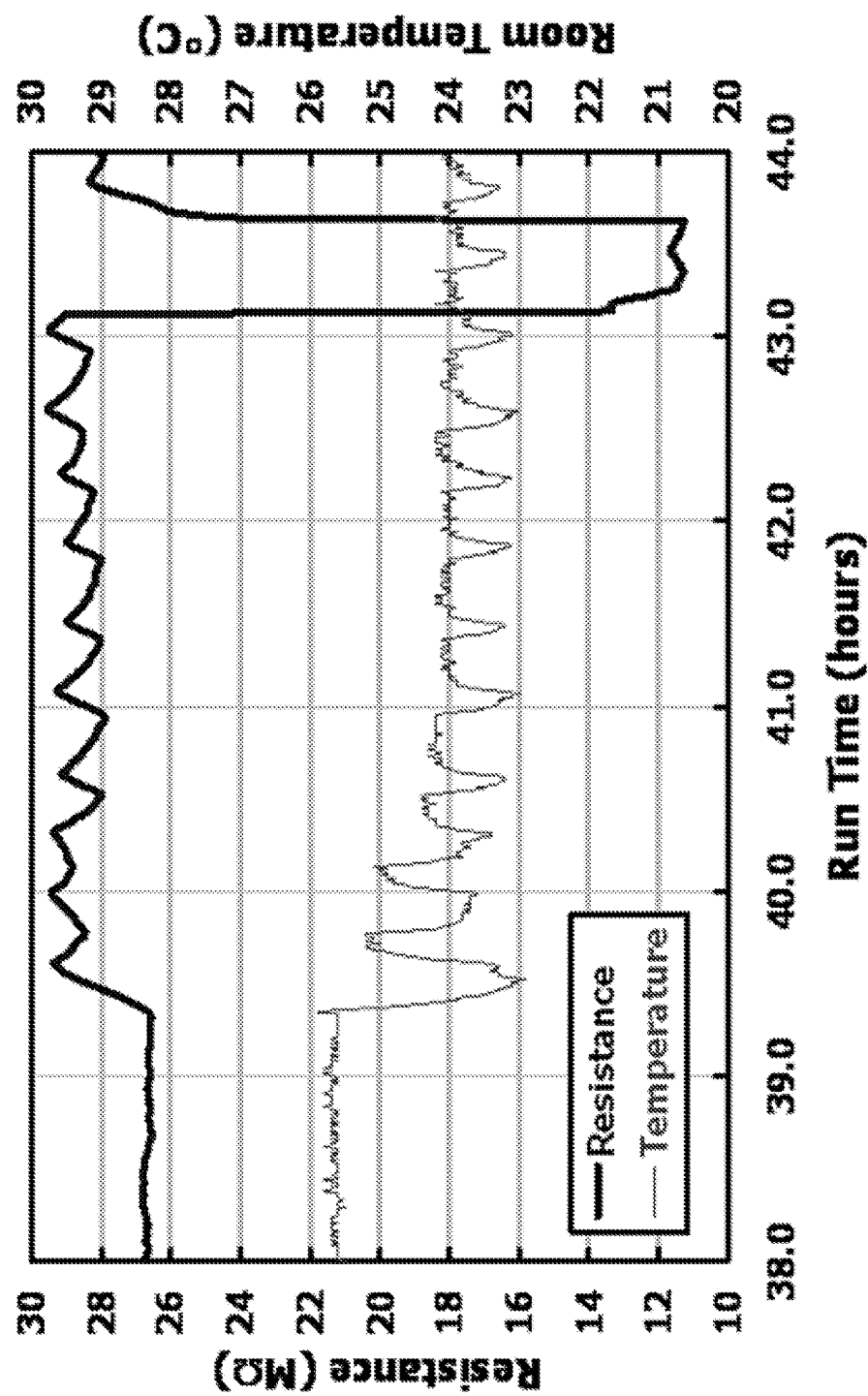
FIG. 28 is a graph of the effect of ambient temperature on the baseline resistance of the $H_2$ sensor of EXAMPLE 21.

It is desirable that the sensor may operate over a wide range of atmospheric conditions without false alarms. While testing sensor prototypes, the room temperature was found to have a significant effect on the baseline resistance of the sensor, as shown in FIG. 28, despite heating of the sensor to a temperature between 175° C. and 225° C. using a NiCr heater. The fluctuations in the room temperature due to the air conditioner cycling on and off were directly correlated to movements in the baseline resistance. The large drop in resistance during hour 43 was a response of the sensor to 1.0% hydrogen. This suggests a shift in temperature may be detected as the presence of hydrogen. A drop in atmospheric temperature may increase the baseline resistance of the sensor and may cause the presence of hydrogen to go undetected.

Such temperature sensitivity issue may be addressed by including a temperature sensor in a sensor control and alarm circuit. A calibration or look-up table may be used to correct for the temperature effect on the baseline sensor resistance.

Figure 29:
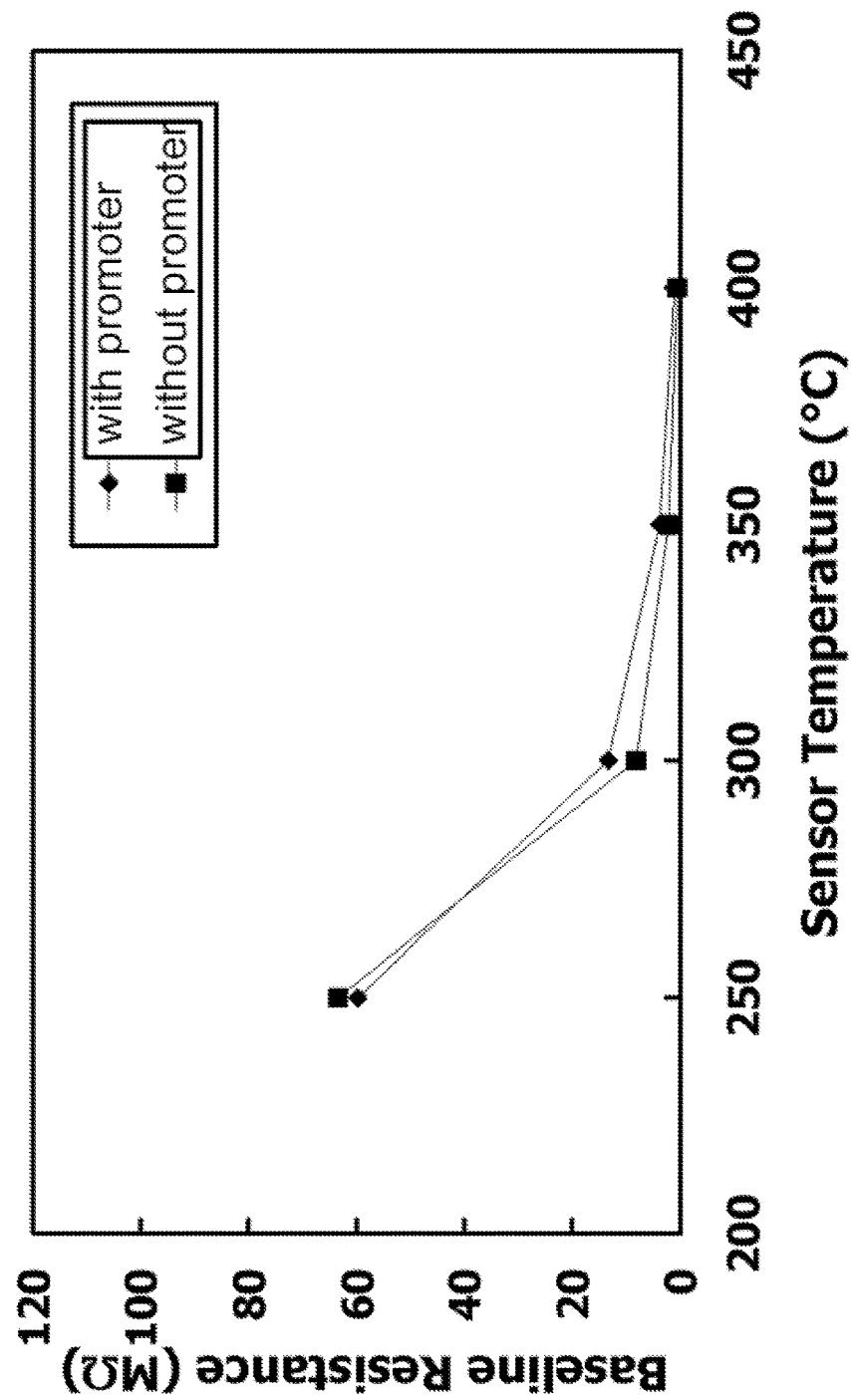
FIG. 29 is a graph of the effect of the promoter on the baseline resistance of the $H_2$ sensor of EXAMPLE 21.

Alternatively, the difference in sensitivity between the sensor material with and without a promoter may be used to compensate for temperature variation, avoiding a separate temperature sensor in the sensor control circuit. A dual sensor element was employed, including two sensors: an active, promoted, hydrogen sensor; and an inactive, unpromoted, hydrogen sensor. FIG. 29 shows that the promoted and unpromoted sensors had the same baseline resistance over a range of temperatures and were affected by changes in atmospheric temperature in the same way. FIG. 6 shows that the unpromoted sensor, however, had a significantly lower sensitivity to hydrogen compared to the promoted sensor, so response of the unpromoted sensor may be used for temperature compensation of the promoted sensor signal. Compensation may be implemented in a sensor control circuit through analog or digital methods including, for example, a Wheatstone bridge circuit, half-bridge Wheatstone bridge circuit, comparator circuit, a microprocessor, and the like.

In addition to providing built-in compensation for the effects of atmospheric temperature on the baseline, the dual sensor element may contribute to the overall stability of the sensor by canceling cross sensitivity. As described herein, the addition of palladium to the sensor selectively increased the sensitivity to hydrogen relative to various cross sensitivities. While almost all of the cross sensitivity to CO and $CH_4$ may be tuned out by adjusting the operating temperature, the sensor may still exhibit small changes in resistance in the presence of these gases. Because the palladium does not have much impact on those responses, both the promoted sensor and the unpromoted sensor may be expected to undergo similar changes in resistance in the presence of interfering gases such that these changes may be canceled out in an electronic control circuit.

Figure 30:
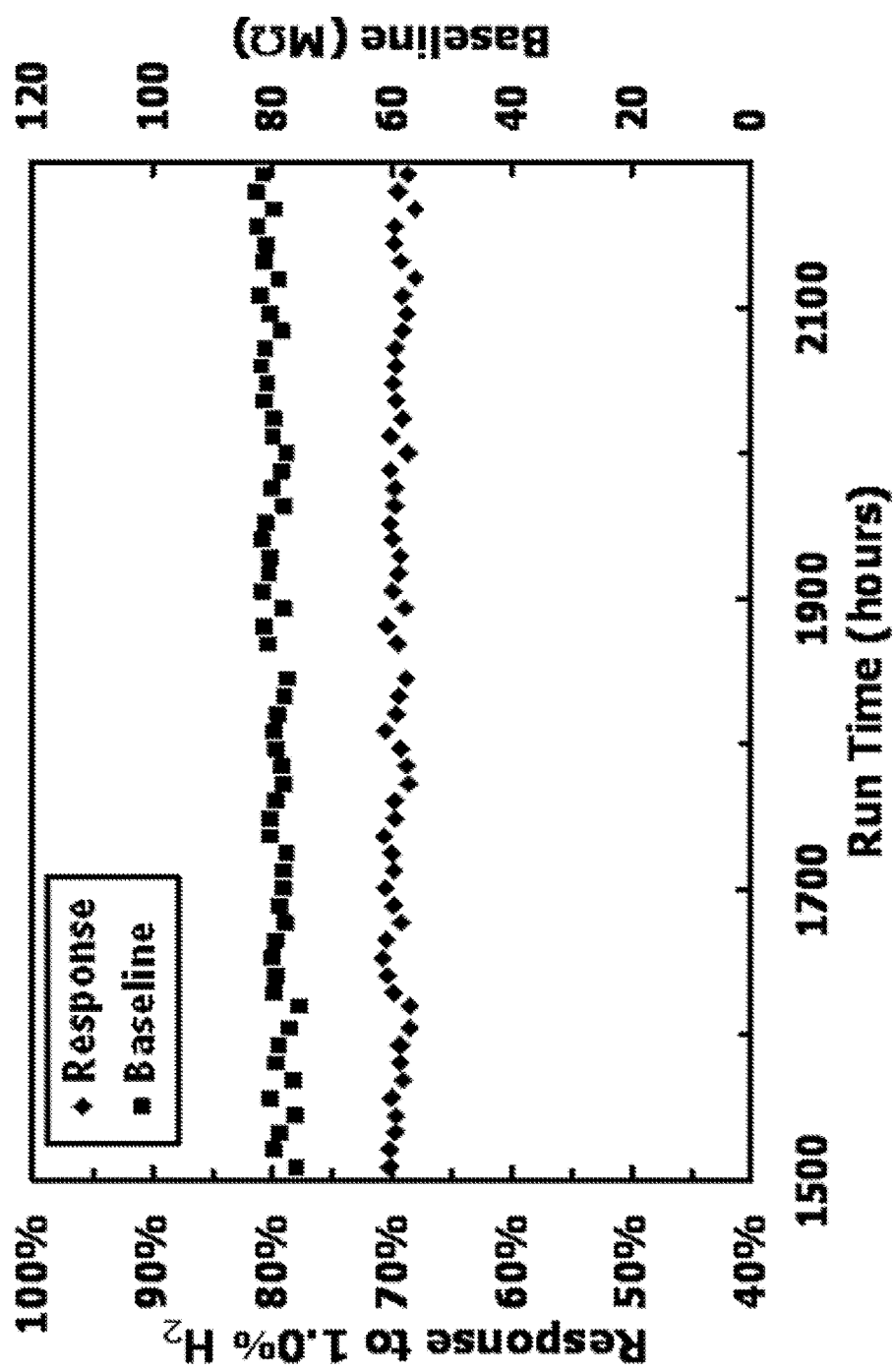
FIG. 30 is a graph of the zero and span drift of the $H_2$ sensor of EXAMPLE 21 at 175° C.

The dual sensor element may also contribute to the overall stability of the sensor by canceling zero drift. For example, when the sensor was operated at lower power levels and lower temperatures, a finite amount of baseline resistance drift was observed. FIG. 30 shows the final 700 hours of a long-term test. After three months of testing, the drift in the baseline was less than $5\times10^{-3}$ MΩ/hr. Without wishing to be bound by theory, it is believed that the observed zero drift may be an artifact of the ceramic sensor and not due to the palladium promoter. An unpromoted sensor may match the zero drift of the promoted sensor and serve to further stabilize the sensor signal.

The second, unpromoted sensor may add increased bulk and cost of the overall assembly. Both the promoted and unpromoted sensors may be housed within the flame arrestor due to the elevated temperature of the NiCr heater. However, the size of the sensor elements may be reduced through improved manufacturing capabilities, by locating both the promoted and unpromoted sensors on the same tube support sharing a common electrode in the middle, and the like.

Both sensors may be heated, doubling the power used. However, reducing the size of the sensor elements and/or locating the promoted and unpromoted sensors on the same tube may reduce the power used.

The dual sensor may benefit from consistency of baseline resistance from sensor to sensor. Part-to-part consistency may be achieved through optimization of manufacturing processes. Alternatively, an initial calibration of the baseline resistance of the promoted and unpromoted sensors may be used.

The tubular sensor device with dual sensor elements yielded highly satisfactory results in combination with the hydrogen-sensitive composite material of the present invention. Each element may also yield satisfactory results when used independently or in subcombinations of less than all of the demonstrated combination of elements. For example, the hydrogen-sensitive composite may be useful in devices having other than tubular configurations.

In addition, the tubular sensor device with dual sensor element may be useful with sensor coatings for detecting other gases, including but not limited to carbon monoxide, methane, hydrogen sulfide, sulfur oxides, nitrogen oxides, humidity, and ammonia. Such devices may be expected to have improved baseline resistance, e.g., when the gas sensor materials may be susceptible to environmental effects.

Embodiments described herein may be achieved by many techniques and methods known to persons who are skilled in this field. To those skilled and knowledgeable in the arts to which the present invention pertains, many widely differing embodiments will be suggested by the foregoing without departing from the intent and scope of the present invention. The descriptions and disclosures herein are intended solely for purposes of illustration and should not be construed as limiting the scope of the present invention which is described by the following claims.

To the extent that the term "include" or "including" is used in the specification or the claims, it is intended to be inclusive in a manner similar to the interpretation of the term "comprising" when employed as a transitional word in a claim. Furthermore, to the extent that the term "or" is employed (e.g., A or B) it is intended to mean "A or B or both." When "only A or B but not both" is intended, then the term "only A or B but not both" will be employed. Thus, use of the term "or" herein is the inclusive, and not the exclusive use. As used in the specification and the claims, the singular forms "a," "an," and "the" include the plural. As used herein, the term "approximately" means plus or minus 10% unless otherwise specified.

The terms "optional" and "optionally" mean that the subsequently described circumstance may or may not occur, so that the description includes instances where the circumstance occurs and instances where it does not.

While the present application has been illustrated by the description of embodiments, and while the embodiments have been described in considerable detail, it is not the intention to restrict or in any way limit the scope of the appended claims to such detail. Additional advantages and modifications will readily appear to those skilled in the art, having the benefit of this application. Therefore, the application, in its broader aspects, is not limited to the specific details and illustrative examples shown. Departures may be made from such details and examples without departing from the spirit or scope of the general inventive concept.

The invention claimed is:

1. A method for detecting molecular hydrogen ($H_2$), comprising:
   providing a gas comprising $H_2$;
   providing a $H_2$-selective porous composite, the $H_2$-selective porous composite comprising cerium oxide, the $H_2$-selective porous composite being characterized by a percentage by weight of the cerium oxide of at least about 94%;
   contacting the gas comprising $H_2$ to the $H_2$-selective porous composite; and
   selectively detecting $H_2$ in the gas comprising $H_2$ according to a decrease in an electrical resistance of the $H_2$-selective porous composite.

2. The method of claim 1, the cerium oxide being undoped cerium oxide.

3. The method of claim 1, the $H_2$-selective porous composite further comprising a metal oxide modifier, the metal oxide modifier comprising one or more of: tin oxide, indium oxide, titanium oxide, copper oxide, cobalt oxide, tungsten oxide, molybdenum oxide, nickel oxide, iron oxide, niobium oxide, vanadium oxide, and a transition metal oxide.

4. The method of claim 3, the $H_2$-selective porous composite being characterized by a percentage by weight of the metal oxide modifier of up to about 5%.

5. The method of claim 1, the $H_2$-selective porous composite being characterized by a percentage by weight of cerium oxide of at least about 95%.

6. The method of claim 1, selectively detecting the $H_2$ comprising detecting the $H_2$ at a level in the gas comprising $H_2$ of at least about 0.1%.

7. The method of claim 1, comprising selectively detecting $H_2$ in the gas comprising $H_2$ at a temperature of at least about 400° C.

8. The method of claim 1, the $H_2$-selective porous composite, when characterized at a temperature range of from about 400° C. to about 600° C. in simulated air at 0% relative humidity, comprising one or more of:
   a percent sensitivity of at least about 22% to 1% $H_2$ in the simulated air;
   a relative percent sensitivity of at least about 15% for 1% $H_2$ relative to 200 ppm carbon monoxide in the simulated air; and a relative percent sensitivity of at least about 2% for 1% $H_2$ relative to 0.5% methane in the simulated air.

9. The method of claim 1, the $H_2$-selective porous composite comprising a response time of less than about ten seconds to reach about 90% of a maximum change in the electrical resistance when characterized at a temperature of about 400° C. in simulated air at 0% relative humidity, the response time starting upon introduction of 1% $H_2$ to the simulated air.

10. The method of claim 1, the $H_2$-selective porous composite comprising a noble metal promoter comprising one or more of: palladium, ruthenium, platinum, gold, rhodium, and iridium.

11. The method of claim 10, the $H_2$-selective porous composite comprising at least about 1 wt % of the noble metal promoter.

12. The method of claim 1, the $H_2$-selective porous composite substantially excluding a noble metal promoter.

13. The method of claim 1, the $H_2$-selective porous composite comprising:
the cerium oxide in the form of undoped cerium oxide;
a metal oxide modifier in contact with the undoped cerium oxide, the metal oxide modifier being present in an amount of up to about 5 wt % of the $H_2$-selective porous composite; and
a noble metal promoter in contact with the undoped cerium oxide, the noble metal promoter being present in an amount of up to about 1 wt % of the $H_2$-selective porous composite.

14. The method of claim 1, the $H_2$-selective porous composite characterized by:
the cerium oxide being in the form of undoped cerium oxide;
about 5 wt % of tin oxide in contact with the undoped cerium oxide; and
about 1 wt % of palladium in contact with the undoped cerium oxide.

15. A kit for detecting molecular hydrogen ($H_2$), comprising:
a $H_2$ gas sensor device, comprising:
a support;
electrodes on a first surface of the support; and
a $H_2$-selective porous composite coated on the first surface of the support:
$H_2$-selective porous composite being characterized by a percentage by weight of at least about 94% of a ceria composition that is one of: doped cerium oxide and undoped cerium oxide, and
the $H_2$-selective porous composite contacting the electrodes such that an electrical resistance of the $H_2$-selective porous composite is measurable at the electrodes,
provided that when the ceria composition is gadolinium doped ceria and the $H_2$-selective porous composite excludes a noble metal promoter, the $H_2$-selective porous composite comprises indium oxide, copper oxide, cobalt oxide, nickel oxide, iron oxide, niobium oxide, or vanadium oxide;
instructions, the instructions comprising:
directions to contact a gas comprising $H_2$ to the $H_2$-selective porous composite of the $H_2$ gas sensor device; and
directions to selectively detect $H_2$ in the gas comprising $H_2$ by measuring a decrease in the electrical resistance of the $H_2$-selective porous composite at the electrodes.

16. The kit of claim 15, the support comprising one or more of: aluminum oxide, yttrium-stabilized zirconia, cerium oxide, gadolinium-doped ceria, magnesium aluminate, and magnesium oxide.

17. The kit of claim 15, the $H_2$ gas sensor device further comprising an integral resistive heater.

18. The kit of claim 17, the instructions further comprising directions to vary an electrical resistance of the resistive heater to control a sensitivity of the $H_2$ gas sensor device to relative humidity.

19. The kit of claim 17, the support comprising one of:
a micro-tubular support, the resistive heater being located in the interior of the micro-tubular support; and
a planar support, the resistive heater being located on a second surface of the support opposite the first surface of the support.

20. The kit of claim 15, the ceria composition being undoped cerium oxide.

21. The kit of claim 15, the $H_2$-selective porous composite further comprising a metal oxide modifier, the metal oxide modifier comprising one or more of: tin oxide, indium oxide, titanium oxide, copper oxide, cobalt oxide, tungsten oxide, molybdenum oxide, nickel oxide, iron oxide, niobium oxide, vanadium oxide, and a transition metal oxide.

22. The kit of claim 21, the $H_2$-selective porous composite being characterized by a percentage by weight of the metal oxide modifier of up to about 5%.

23. The kit of claim 15, the $H_2$-selective porous composite being characterized by a percentage by weight of cerium oxide of at least about 95%.

24. The kit of claim 15, the instructions comprising directions to selectively detect the $H_2$ at a level in the gas comprising $H_2$ of at least about 0.1%.

25. The kit of claim 15, the instructions comprising directions to selectively detect the $H_2$ in the gas comprising $H_2$ at a temperature of at least about 400° C.

26. The kit of claim 15, the $H_2$-selective porous composite, when characterized at a temperature range of from about 400° C. to about 600° C. in simulated air at 0% relative humidity, comprising one or more of:
a percent sensitivity of at least about 22% to 1% $H_2$ in the simulated air;
a relative percent sensitivity of at least about 15% for 1% $H_2$ relative to 200 ppm carbon monoxide in the simulated air; and
a relative percent sensitivity of at least about 2% for 1% $H_2$ relative to 0.5% methane in the simulated air.

27. The kit of claim 15, the $H_2$-selective porous composite comprising a response time of less than about ten seconds to reach about 90% of a maximum change in the electrical resistance when characterized at a temperature of about 400° C. in simulated air at 0% relative humidity, the response time starting upon introduction of 1% $H_2$ to the simulated air.

28. The kit of claim 15, the $H_2$-selective porous composite comprising the noble metal promoter comprising one or more of: palladium, ruthenium, platinum, gold, rhodium, and iridium.

29. The kit of claim 28, the $H_2$-selective porous composite comprising at least about 1 wt % of the noble metal promoter.

30. The kit of claim 15, the $H_2$-selective porous composite substantially excluding the noble metal promoter.

31. The kit of claim 15, the $H_2$-selective porous composite comprising:
the ceria composition in the form of undoped cerium oxide;

a metal oxide modifier in contact with the undoped cerium oxide, the metal oxide modifier being present in an amount of up to about 5 wt % of the $H_2$-selective porous composite; and the noble metal promoter in contact with the undoped cerium oxide, the noble metal promoter being present in an amount of up to about 1 wt % of the $H_2$-selective porous composite.

32. The kit of claim 15, the $H_2$-selective porous composite characterized by:

the ceria composition being in the form of undoped cerium oxide;

about 5 wt % of tin oxide in contact with the undoped cerium oxide; and further comprising about 1 wt % of palladium in contact with the undoped cerium oxide.

33. A molecular hydrogen ($H_2$) gas sensor device, comprising:

a support;

electrodes on a first surface of the support; and a $H_2$-selective porous composite coated on the first surface of the support:

the $H_2$-selective porous composite being characterized by a percentage by weight of at least about 94% of a ceria composition that is one of: doped cerium oxide and undoped cerium oxide, the $H_2$-selective porous composite contacting the electrodes such that an electrical resistance of the $H_2$-selective porous composite is measurable at the electrodes, and the $H_2$-selective porous composite comprising a metal oxide modifier in contact with the ceria composition, the metal oxide modifier being present in an amount of up to about 5 wt % of the $H_2$-selective porous composite, provided that when the ceria composition is gadolinium doped ceria and the $H_2$-selective porous composite excludes a noble metal promoter, the metal oxide modifier comprises indium oxide, copper oxide, cobalt oxide, nickel oxide, iron oxide, niobium oxide, or vanadium oxide.

34. The $H_2$ gas sensor device of claim 33, the support comprising one or more of: aluminum oxide, yttrium-stabilized zirconia, cerium oxide, gadolinium-doped ceria, magnesium aluminate, and magnesium oxide.

35. The $H_2$ gas sensor device of claim 33, the $H_2$ gas sensor device further comprising an integral resistive heater.

36. The $H_2$ gas sensor device of claim 35, the support comprising one of:

a micro-tubular support, the resistive heater being located in the interior of the micro-tubular support; and a planar support, the resistive heater being located on a second surface of the support opposite the first surface of the support.

37. The $H_2$ gas sensor device of claim 33, the metal oxide modifier comprising one or more of: tin oxide, indium oxide, titanium oxide, copper oxide, cobalt oxide, tungsten oxide, molybdenum oxide, nickel oxide, iron oxide, niobium oxide, vanadium oxide, and a transition metal oxide.

38. The $H_2$ gas sensor device of claim 33, the $H_2$-selective porous composite being characterized by a percentage by weight of the metal oxide modifier of up to about 2.5%.

39. The $H_2$ gas sensor device of claim 33, the $H_2$-selective porous composite being characterized by a percentage by weight of the ceria composition of at least about 95%.

40. The $H_2$ gas sensor device of claim 33, the ceria composition being undoped cerium oxide.

41. The $H_2$ gas sensor device of claim 33, the $H_2$-selective porous composite comprising the noble metal promoter comprising one or more of: palladium, ruthenium, platinum, gold, rhodium, and iridium.

42. The $H_2$ gas sensor device of claim 41, the $H_2$-selective porous composite comprising at least about 1 wt % of the noble metal promoter.

43. The $H_2$ gas sensor device of claim 33, the $H_2$-selective porous composite substantially excluding the noble metal promoter.

44. The $H_2$ gas sensor device of claim 33, the $H_2$-selective porous composite comprising:

the ceria composition in the form of undoped cerium oxide;

the metal oxide modifier in contact with the undoped cerium oxide, the metal oxide modifier being present in an amount of up to about 5 wt % of the $H_2$-selective porous composite; and the noble metal promoter in contact with the undoped cerium oxide, the noble metal promoter being present in an amount of up to about 1 wt % of the $H_2$-selective porous composite.

45. The $H_2$ gas sensor device of claim 33, the $H_2$-selective porous composite characterized by:

the ceria composition being in the form of undoped cerium oxide;

about 5 wt % of tin oxide in contact with the undoped cerium oxide; and about 1 wt % of palladium in contact with the undoped cerium oxide.

46. A composition, comprising:

a molecular hydrogen ($H_2$)-selective porous composite comprising:

a percentage by weight of at least about 94% of a ceria composition that is one of: doped cerium oxide and undoped cerium oxide, a metal oxide modifier in contact with the ceria composition, the metal oxide modifier being present in an amount of up to about 5 wt % of the $H_2$-selective porous composite, provided that when the ceria composition is gadolinium doped ceria and the $H_2$-selective porous composite excludes a noble metal promoter, the metal oxide modifier comprises indium oxide, copper oxide, cobalt oxide, nickel oxide, iron oxide, niobium oxide, or vanadium oxide.

47. The composition of claim 46, the metal oxide modifier comprising one or more of: tin oxide, indium oxide, titanium oxide, copper oxide, cobalt oxide, tungsten oxide, molybdenum oxide, nickel oxide, iron oxide, niobium oxide, vanadium oxide, and a transition metal oxide.

48. The composition of claim 46, the $H_2$-selective porous composite being characterized by a percentage by weight of the metal oxide modifier of up to about 2.5%.

49. The composition of claim 46, the $H_2$-selective porous composite being characterized by a percentage by weight of the ceria composition of at least about 95%.

50. The composition of claim 46, the ceria composition being undoped cerium oxide.

51. The composition of claim 50, the $H_2$-selective porous composite comprising the noble metal promoter comprising one or more of: palladium, ruthenium, platinum, gold, rhodium, and iridium.

52. The composition of claim 51, the $H_2$-selective porous composite comprising at least about 1 wt % of the noble metal promoter.

53. The composition of claim 46, the $H_2$-selective porous composite substantially excluding the noble metal promoter.

54. The composition of claim 46, the $H_2$-selective porous composite comprising:
   the ceria composition in the form of undoped cerium oxide;
   the metal oxide modifier in contact with the undoped cerium oxide, the metal oxide modifier being present in an amount of up to about 5 wt % of the $H_2$-selective porous composite; and
   further comprising the noble metal promoter in contact with the undoped cerium oxide, the noble metal promoter being present in an amount of up to about 1 wt % of the $H_2$-selective porous composite.

55. The composition of claim 46, the $H_2$-selective porous composite characterized by:
   the ceria composition being in the form of undoped cerium oxide;
   about 5 wt % of tin oxide as the metal oxide modifier in contact with the undoped cerium oxide; and
   further comprising about 1 wt % of palladium in contact with the undoped cerium oxide.

\* \* \* \* \*